US012693281B2

(12) United States Patent
Studer et al.

(10) Patent No.: US 12,693,281 B2
(45) Date of Patent: Jul. 28, 2026

(54) GAS DETECTION DEVICE AND GAS DETECTION PROCESS WITH AUTOMATIC NOISE COMPENSATION

(71) Applicant: Dräger Safety AG & Co. KGaA, Lübeck (DE)

(72) Inventors: Matthias Studer, Lübeck (DE); Jürgen Osswald, Lübeck (DE); Tom Pöthig, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 329 days.

(21) Appl. No.: 18/321,036

(22) Filed: May 22, 2023

(65) Prior Publication Data
US 2023/0375516 A1 Nov. 23, 2023

(30) Foreign Application Priority Data
May 23, 2022 (DE) ..................... 10 2022 112 865.2

(51) Int. Cl.
G01N 33/00 (2006.01)

(52) U.S. Cl.
CPC ..... G01N 33/0031 (2013.01); G01N 33/0011 (2013.01); G01N 33/0063 (2013.01); G01N 33/0067 (2013.01); G01N 33/0073 (2013.01)

(58) Field of Classification Search
CPC ........... G01N 33/0031; G01N 33/0011; G01N 33/0063; G01N 33/0067; G01N 33/0073;
(Continued)

(56) References Cited

U.S. PATENT DOCUMENTS

| | | | |
|---|---|---|---|
| 4,875,406 A | 10/1989 | Hoelter et al. | |
| 5,234,837 A * | 8/1993 | Accorsi ................... | G01N 27/16 |
| | | | 73/23.31 |

(Continued)

FOREIGN PATENT DOCUMENTS

| | | | | |
|---|---|---|---|---|
| CN | 101073007 A * | 11/2007 | ............. | G01N 27/00 |
| CN | 106662559 A * | 5/2017 | ......... | G01N 33/0037 |

(Continued)

OTHER PUBLICATIONS

JP-2017142274-A (Year: 2017).*
(Continued)

*Primary Examiner* — Fatemeh Esfandiari Nia
(74) *Attorney, Agent, or Firm* — McGlew and Tuttle, P.C.

(57) ABSTRACT

A device and process monitor a spatial area for a target gas. A sensor of the gas detection device used has a detection variable ($\Delta U_{korr,0}$) that is affected by the concentration of target gas. A detection variable sensor measures this detection variable ($\Delta U_{korr,0}$). The influence of a slower influencing variable and of a faster influencing variable, on the detection variable ($\Delta U_{korr,0}$), are computationally compensated to determine an influence-corrected detection variable ($\Delta U_{korr,1}$). Depending on the influence-corrected detection variable ($\Delta U_{korr,1}$), the target gas concentration is determined. For computational compensation, the time course ($Dr[\Delta U_{korr,0}]$) of the respective influence of the two influencing variables is estimated, for which a measurement value series from the detection variable sensor is used. The time course ($Dr[\Delta U_{korr,0}]$) is determined in such a way that the change per time unit of the influence lies within a given change tolerance band ($Dr'[\Delta U_{korr,0}]_{min}$, $Dr'[\Delta U_{korr,0}]_{max}$) for this influencing variable.

20 Claims, 9 Drawing Sheets

(58) Field of Classification Search
CPC ............... G01N 33/0006; G01N 27/16; G01N
33/0047; G01N 33/00–0075; G06F
18/217
See application file for complete search history.

(56) References Cited

U.S. PATENT DOCUMENTS

| | | | |
|---|---|---|---|
| 2005/0228596 A1 | 10/2005 | Shoji | |
| 2006/0155486 A1* | 7/2006 | Walsh | G01N 33/0034 |
| | | | 702/32 |
| 2009/0035184 A1* | 2/2009 | Koda | G01N 27/16 |
| | | | 422/94 |
| 2013/0059395 A1 | 3/2013 | Alvarez et al. | |
| 2020/0088669 A1* | 3/2020 | König | G01N 33/0062 |
| 2020/0333308 A1* | 10/2020 | Billat | G01N 25/18 |
| 2020/0393432 A1* | 12/2020 | Swanson | G01N 27/404 |
| 2021/0285907 A1 | 9/2021 | Makaram et al. | |

| | | | | |
|---|---|---|---|---|
| 2022/0252567 A1* | 8/2022 | Yanni | | G01N 33/004 |
| 2022/0326169 A1 | 10/2022 | Osswald et al. | | |
| 2022/0381731 A1* | 12/2022 | Rogers | | G01N 27/121 |

FOREIGN PATENT DOCUMENTS

| | | | | | |
|---|---|---|---|---|---|
| CN | 109507140 B | * | 4/2020 | ............. | G01N 21/01 |
| DE | 102017005713 A1 | * | 12/2018 | ............. | G01N 27/16 |
| DE | 102022106689 A1 | | 10/2022 | | |
| GB | 2604041 A | | 8/2022 | | |
| JP | 2013503998 A | * | 2/2013 | ......... | F02D 41/2435 |
| JP | 2017142274 A | * | 8/2017 | | |

OTHER PUBLICATIONS

DE-102017005713-A1 (Year: 2018).*
CN-101073007-A (Year: 2007).*
CN-106662559-A (Year: 2017).*
CN-109507140-B (Year: 2020).*
JP-2013503998-A (Year: 2013).*

* cited by examiner

GAS DETECTION DEVICE AND GAS DETECTION PROCESS WITH AUTOMATIC NOISE COMPENSATION

CROSS REFERENCE TO RELATED APPLICATIONS

This application claims the benefit of priority under 35 U.S.C. § 119 of German Application 10 2022 112 865.2, filed May 23, 2022, the entire contents of which are incorporated herein by reference.

TECHNICAL FIELD AND BACKGROUND

The invention relates to a device and a process for automatically monitoring a spatial area for at least one predetermined target gas. The target gas or at least one target gas is in particular a combustible target gas.

SUMMARY

An object of the invention is to provide a gas detection device and process configured to monitor a spatial area for at least one predetermined target gas and to operate with greater reliability than known devices and processes.

The task is solved by a gas detection device having gas detection device features according to the invention and by a gas detection process having gas detection process features according to the invention. Advantageous embodiments of the gas detection device according to the invention are, as far as useful, also advantageous embodiments of the gas detection process according to the invention, and vice versa advantageous embodiments of the gas detection process according to the invention are also advantageous embodiments of the gas detection device according to the invention.

The gas detection device according to the invention and the gas detection process according to the invention are capable of monitoring a spatial area for at least one predetermined target gas. The spatial area to be monitored is, for example, a production plant or the interior of a building or vehicle or aircraft. The or at least one target gas to be detected is in particular a combustible target gas, for example methane ($CH_4$). In the following the term "target gas" is used. This term can denote several target gases which occur or can occur simultaneously in this spatial area to be monitored.

The gas detection device comprises a sensor unit with a sensor. The sensor has a measurable detection variable, in particular the electrical voltage or current or electrical charge of the sensor or other electrical detection variable. This detection variable is influenced by the concentration of target gas in the spatial area to be monitored. The detection variable can be described as an indicator for the target gas concentration. In the case of multiple target gases, the detection variable is influenced by the sum of the target gas concentrations.

The sensor unit further comprises a detection variable sensor. The detection variable sensor is able to measure an indicator for the detection variable of the sensor, whereby this detection variable is influenced by the target gas concentration, i.e. its value depends on the target gas concentration. The detection variable sensor is further capable of automatically generating a measurement value series (a series over time of measured values of the detection variable) which describes the temporal course of the detection variable. For this generation, the detection variable sensor uses the result of several measurements of the detection variable at different times (sample time points), i.e. uses several measured values.

In the following, the terms "influencing variable", "slower influencing variable" and "faster influencing variable" are used. An "influencing variable" is understood to be a physical variable (physical quantity) that occurs or can occur in the spatial area to be monitored or in the gas detection device itself, independently of the target gas or a target gas to be detected, and which influences or can influence the detection variable. Examples for the influencing variable include temperature, humidity, and pressure in the spatial area or a change (drift) in the sensor unit, for example due to aging or sensor pollution. The respective influence of every influencing variable additively overlaps with the influence of the target gas concentration on the detection variable. By "faster" and "slower" it is meant that one influencing variable has a slower effect on the detection variable than the other influencing variable, i.e. the slower influencing variable is able to cause a smaller maximum change per time unit than the faster influencing variable.

The gas detection device further comprises a signal-processing influencing variable estimator. Preferably, this influencing variable estimator is implemented as software being executed or executable on a control unit. The influencing variable estimator is capable of compensating, at least approximately, computationally (by calculation) both the influence of a slower influencing variable and the influence of a faster influencing variable on the detection variable, and does so automatically. These two influencing variables occur in the spatial area to be monitored independently of the target gas or each target gas to be detected and preferably exert influence on the detection variable independently of each other. For computational compensation, the influencing variable estimator uses the measurement value series generated by the detection variable sensor. Through computational compensation, the influencing variable estimator generates an influence-corrected detection variable, i.e. a detection variable in which the respective influence of both influencing variables on the measured detection variable is at least approximately computationally compensated.

Furthermore, the gas detection device comprises a signal-processing evaluation unit. The evaluation unit is configured to automatically decide whether the target gas or at least one target gas to be detected is present in the area to be monitored. Alternatively, or additionally, the evaluation unit is configured to determine the concentration of the target gas or at least one target gas to be detected in the spatial area to be monitored, in case of several target gases at least the sum of the target gas concentrations. For this decision and/or concentration determination, the evaluation unit automatically uses at least one value of the influence-corrected detection variable, optionally several values of the influence-corrected detection variable for different sampling times.

The gas detection process according to the invention is carried out using such a gas detection device.

The following parameters are predefined:

a narrower change tolerance band, which describes a possible change per time unit of the detection variable due to the influence of the slower influencing variable on the detection variable, and a wider change tolerance band describing a possible change per time unit of the detection variable due to the influence of the faster influencing variable on the detection variable.

Both change tolerance bands are or comprise one respective interval. The two boundaries (thresholds) of this interval preferably have as a unit of measurement the change per time unit of the unit of measurement of the detection variable. The narrower change tolerance band is narrower than the wider change tolerance band, i.e., the distance between the two interval boundaries is smaller. The narrower change tolerance band is included in (is a subset of) the wider change tolerance band.

In addition, a value range is predefined, namely a value range for the faster influencing variable. The value range also is or includes an interval. This value range is also called the "narrower value range". The narrower value range is predefined such that the values of the impact of the faster influencing variable lie within this value range. With other words: The possible deviation (variation, change) of the detection variable due to the influence of the faster influencing variable on the detection variable lies within the narrower value range.

The gas detection apparatus according to the invention is configured to perform the following steps, and the gas detection process according to the invention comprises the following steps:

The influencing variable estimator determines an estimated time course of the influence of the slower influencing variable on the detection variable—or on the detection variable already adjusted for the influence of the faster influencing variable. The temporal change per time unit of the estimated time course lies in the given narrower change tolerance band.

The influencing variable estimator determines an estimated time course of the influence of the faster influencing variable on the detection variable—or on the detection variable already adjusted for the influence of the slower influencing variable. The change per time unit of the estimated time course lies within the specified wider (broader) change tolerance band. Furthermore, each value of the estimated time course of the influence of the faster influencing variable lies in the specified value range for the faster influencing variable (narrower value range).

For these two determinations, the influencing variable estimator uses the measurement value series from the detection variable sensor—or a measurement value series derived from the measurement value series from the detection variable sensor, which derivation is predefined in embodiments.

To compensate for the influence of the slower influencing variable on the detection variable, the influencing variable estimator subtracts the estimated time course of the slower influencing variable from the original detection variable or from the detection variable adjusted for the influence of the faster influencing variable.

To compensate for the influence of the faster influencing variable on the detection variable, the influencing variable estimator subtracts the estimated time course of the faster influencing variable from the original detection variable or from the detection variable adjusted for the influence of the slower influencing variable.

Therefore, in total, the influencing variable estimator performs two compensation steps in succession or in parallel.

In accordance with the determinations, the detection variable is influenced by the concentration of the target gas or at least one target gas. As a rule, it cannot be avoided that the detection variable is also influenced by other influencing variables. These influencing variables include, for example, aging (drift) of the sensor, ambient pressure (air pressure), ambient humidity (air humidity) and/or a variable ambient temperature (air temperature). Which influencing variables can actually affect the detection variable in a relevant way often depends on which measurement principle the sensor uses for the detection variable, and sometimes also on the environment in which the gas detection device is used. According to the invention, the influence of at least two influencing variables on the detection variable is compensated at least approximately by calculation, optionally additionally the influence of at least one further influencing variable. The step of compensating the influence of an influencing variable by calculation is also referred to as the step of computationally adjusting the detection variable by this influencing variable (compensating for this influence).

According to the invention, a time course of the influencing variable is estimated for each influencing variable whose influence is compensated by calculation. The time course of an influencing variable on the detection variable is understood to be the deviation between the actual time course of the detection variable and the time course that the detection variable would have if this influencing variable were not present and therefore did or could not affect the detection variable. This deviation and the estimation refer to a situation in which no given target gas influences (affects) the detection variable.

According to the invention this temporal course of an influencing variable is estimated, for which estimation a measurement value series with measured values of the actual detection variable is used. Alternatively, a measurement value series with measured values of the detection variable, which has already been adjusted for the influence of another influencing variable, is used. The feature according to the invention of estimating the influence of an influencing variable eliminates the need to provide a sensor for this influencing variable and to use a signal from this sensor to eliminate the influence of an influencing variable on the detection variable computationally or otherwise. One example: In order to compensate according to the invention the influencing variable ambient temperature onto the detection variable, it is possible, but thanks to the invention in many cases not necessary, that the gas detection device comprises a sensor for the ambient temperature.

As a rule, a gas detection device comprises a sensor in the form of a measuring unit on which the detection variable occurs. Gas detection devices have become known which, in addition to the measuring component, comprise a reference unit, the reference unit also having the detection variable. The detection variable of the measuring unit is influenced by the target gas or at least one target gas as well as by at least one influencing variable. The detection variable of the reference unit is influenced by the same influencing variables as those of the measurement component, but ideally not at all by a target gas to be detected. Ideally, therefore, the difference between the two detection variables is influenced only by the target gas, but not by an influencing variable. In particular, the ambient temperature ideally has the same effect on the two detection variables. In practice, however, it is usually unavoidable that at least one influencing variable has a different effect on the two units and/or the or one target gas also affects the detection variable of the reference unit.

The invention can also be used for a gas detection device with a reference unit in addition to the measuring unit. In this case, the invention makes it possible to computationally compensate for such influences of influencing variables which act or can act differently on the detection variable of the reference unit than on the detection variable of the measuring unit. In particular, the invention makes it possible to computationally compensate for the influence resulting from the fact that the reference unit differs from the measurement unit due to its configuration and/or ages differently than the measurement unit. If the invention is used in combination with a reference unit, the invention thus makes it possible in many cases to allow larger material tolerances and/or larger manufacturing tolerances.

The change of the detection variable due to an influencing variable must be distinguished from the change of the detection variable due to at least one given target gas. The target gas is to be detected, whereas the influence of the influencing variable is undesired but often unavoidable. For this computational compensation of an influencing variable, the fact is exploited that the detection variable usually changes more rapidly under the influence of a target gas than under the influence of an influencing variable to be compensated. Therefore, a change tolerance band is predefined for each influencing variable whose influence is to be computationally compensated. The change tolerance band for an influencing variable defines an upper threshold and a lower threshold for a possible change per time unit of the impact of the influencing variable. The thresholds apply at least when no target gas is present. The unit of measure of the two thresholds is preferably the unit of measure of the detection variable per time unit, for example mV/sec or $m\Omega$/sec. If a detection variable changes faster, i.e., the change is outside the change tolerance band, this faster change is caused by at least one target gas and not, or at least not solely, by an influencing variable. The use of a change tolerance band thus reduces the risk that a target gas is not detected because an influencing variable is compensated too strongly or otherwise incorrectly.

According to the invention, the influence of a slower influencing variable, the influence of a faster influencing variable and optionally the influence of at least one third influencing variable on the detection variable are at least approximately compensated by calculation. The faster influencing variable causes a faster temporal change of the detection variable than the slower influencing variable at least if no target gas is present, and the or at least one optional third influencing variable taken into account causes a faster change of the detection variable than the faster and thus also than the slower influencing variable.

Whether at least one target gas is present or not and optionally which concentration this target gas has, is automatically decided depending on values of a detection variable. As this detection variable, preferably a variable is used which is generated after a computational compensation of both influencing variables, optionally additionally after a computational compensation of the third considered influencing variable or each additionally considered influencing variable. A feature according to the invention reduces the following risk: The step of computationally compensating the influence of the two influencing variables on an initial detection variable results in a given target gas not being detected. Ideally, this risk is completely eliminated. According to the invention, change tolerance bands are specified for the two influencing variables to be compensated, namely different change tolerance bands. The narrower change tolerance band is narrower than the wider change tolerance band and is completely contained in the wider change tolerance band. This means: The distance between the two thresholds (bounds) of the narrower change tolerance band is smaller than the distance between the two thresholds (bounds) of the wider change tolerance band.

The narrower change tolerance band is selected such that even a slow increase in the concentration of the target gas or a target gas will result in a change in the detection variable that is outside the narrower change tolerance band. Therefore, even a slow increase in the target gas concentration is distinguished from the influence of the slower influencing variable, and the gas detection device is also able to detect a slow increase. This effect is particularly desirable when a relatively small amount per time unit of the target gas escapes from a leak or a further aperture and accumulates in the spatial area.

In order to distinguish the influence of the faster influencing variable on the detection variable from the influence of at least one target gas, according to the invention a value range (smaller value range) is additionally specified for the faster influencing variable. Optionally, a value range is also specified for the slower influencing variable. Preferably, the value range for the faster influencing variable lies in the value range for the slower influencing variable. It is also possible to specify a value range only for the faster influencing variable, but not for the slower influencing variable.

The estimated time course of the influence of the faster influencing variable is estimated in such a way that each value lies within the specified value range for the faster influencing variable. The corresponding statement is valid for the influence of the slower influencing variable and for the optional values range for the slower influencing variable. The feature with the value ranges further reduces the risk that as a consequence of the computational compensation at least one target gas is not detected in an erroneous manner. Furthermore, this embodiment allows in many cases a defect or a significant aging of the gas detection device to be detected and a message about this defect to be generated and output in a form that can be perceived by a human.

In an alternative embodiment of the invention, the evaluation unit is able to automatically decide whether or not at least one target gas to be detected is present in the area to be monitored. Optionally, the evaluation unit generates an alarm in the case that the target gas is detected. In an implementation of this alternative, the evaluation unit performs this decision for at least one sampling time, preferably again for each sampling time of a sequence of sampling times. The measurement value series comprises a sequence of measured values, each measured value referring to a respective sampling time, i.e. describing which value the detection variable has at this sampling time.

The embodiment with the sampling times comprises the following steps, which are performed for at least one sampling time, preferably for several sampling times, especially preferably repeated continuously:

The evaluation unit automatically decides whether or not at least one target gas to be detected is present in the area to be monitored at this sampling time. For this purpose, it uses the value at this sampling time of the influence-corrected detection variable determined according to the invention.

The influencing variable estimator only uses the measured value of the measurement value series for this sampling time to compensate for the time course of the influence of the slower influencing variable and the time course of the influence of the faster influencing variable if the evaluation unit has decided that no target gas is present at this sampling time. A measured value that has arisen under the influence of target gas is therefore not used.

The embodiment therefore provides for the value of the influence-corrected detection variable to be determined on a trial basis at this sampling time. If according to this value at least one target gas is present, the value of the measurement value series is not used to compensate the respective influence of the two influencing variables at this sampling time.

This embodiment increases the reliability that the influences of the two influencing variables can be reliably distinguished from the influence of target gas on the detection variable.

If the evaluation unit decides that at a sampling time a target gas to be detected is present, the respective value at this sampling time of the time course of the influence of the two influencing variables is preferably determined by interpolation or extrapolation.

In a preferred embodiment, a cascaded procedure is used to computationally compensate for the influence of the two influencing variables on the detection variable. The following two alternatives of this cascaded procedure are possible:

In a first alternative of this embodiment, in a first step the estimated time course of the influence of the slower influencing variable on the detection variable is subtracted from the detection variable. In a subsequent second step, the estimated time course of the influence of the faster influencing variable on the detection variable is subtracted from the detection variable corrected for the influence of the slower influencing variable, i.e. from the corrected detection variable obtained in the first step.

In a second alternative of this embodiment, in a first step the estimated time course of the influence of the faster influencing variable on the detection variable is subtracted from the detection variable. In a subsequent second step, the estimated time course of the influence of the slower influencing variable on the detection variable is subtracted from the detection variable corrected for the influence of the faster influencing variable, i.e. from the corrected detection variable obtained in the first step.

In many cases, both alternatives of the cascaded approach result in a relatively reliable computational compensation of the influence of the two influencing variables. Ideally, these two alternatives lead to the same result, but in practice they usually lead to different results.

Preferably, the first alternative comprises the following implementation:

The first step, i.e. the step of subtracting the time course of the influence of the slower influencing variable from the detection variable, provides a compensated measurement value series, i.e. a corrected measurement value series being compensated for the influence of the slower influencing variable on the measurement value series.

In the subsequent second step, the estimated time course of the influence of the faster influencing variable on the detection variable is determined using this compensated measurement value series.

Preferably, the second alternative comprises the following implementation:

The first step, i.e. the step of subtracting the time course of the influence of the faster influencing variable from the detection variable, provides a compensated measurement value series, i.e. a corrected measurement value series being compensated for the influence of the faster influencing variable on the measurement value series.

In the subsequent second step, the estimated time course of the influence of the slower influencing variable on the detection variable is determined using this compensated measurement value series.

The original measurement value series generated by the detection variable sensor is thus used indirectly in both implementations, namely to derive the compensated measurement value series.

In an alternative to this cascaded approach, a first phase and a subsequent second phase are performed. In the first phase, both the estimated time course of the influence of the slower influencing variable and the estimated time course of the influence of the faster influencing variable on the detection variable are determined. For this purpose, the measurement value series from the detection variable sensor is used. In the second phase, both the estimated time course of the slower influencing variable and the estimated time course of the faster influencing variable are subtracted from the detection variable, and thus the influence-compensated detection variable is determined.

According to the invention, a value range for the faster influencing variable is predefined. This value range is used in the step of determining the influence of the faster influencing variable on the detection variable. In one embodiment, no value range is predefined for the slower influencing variable. In another embodiment, another value range is predetermined, namely a value range for the slower influencing variable called wider value range. The value range for the faster influencing variable is narrower than the value range for the slower influencing variable and is included in the value range for the slower influencing variable. This feature takes into account the fact that in many cases the slower influencing variable can have a stronger influence on the detection variable over time than the faster influencing variable.

According to the invention, the estimated time course of the influence of the slower influencing variable on the detection variable is determined in such a way that the change per time unit of the influence of the slower influencing variable on the detection variable lies in the predetermined narrower change tolerance band. According to the embodiment with the wider value range, the estimated time course is additionally determined in such a way that each value of the estimated time course of the influence of the slower influencing variable lies in the wider value range, i.e. in the value range for the slower influencing variable. In many cases, this feature further increases the reliability that the influence of the slower influencing variable is distinguished from the influence of target gas on the detection variable.

In one embodiment, the system automatically checks whether the event has occurred that a predefined number of values of the estimated time course of the slower influencing variable are equal to the upper threshold or to the lower threshold of the predefined value range for the slower influencing variable. If this event is detected, a corresponding message is generated and output in a form that can be perceived by a human. One reason: This event is an indication that the influence of the slower influencing variable can no longer be compensated sufficiently reliably by calculation. This embodiment is particularly important if the slower influencing variable causes aging of the sensor unit, in particular of the detection variable sensor, i.e. is not directly due to an external influence. The message allows a user to check the gas detection device and replace the sensor unit or the entire gas detection device if necessary.

According to the invention, both the influence of a slower influencing variable and the influence of a faster influencing variable on the detection variable are compensated for by calculation. In one embodiment, the influence of a third influencing variable is also compensated for by calculation.

This third influencing variable is even faster than the faster influencing variable. The influence of the third influencing variable is computationally compensated for in accordance with the procedure according to the invention. A third change tolerance band is predefined. The wider change tolerance band, i.e. the one for the faster influencing variable, is narrower than the third change tolerance band. In addition, a value range for the third influencing variable is predefined as the third value range. The third change tolerance band and the third value range are used according to the change tolerance band and the value range for the faster influencing variable. It is also possible to additionally compensate the influence of at least a fourth influencing variable by calculation in the same way.

According to the invention, the sensor has a detection variable that is influenced by the concentration of target gas to be detected in the spatial area to be monitored. This detection variable has a zero point (reference point), which is a value that the detection variable assumes when no target gas is present in the area to be monitored. Typically, when no target gas is present, the sensor will provide a zero point that is different from zero. This difference between the zero point and zero may be due to design, manufacturing, and/or aging of the sensor. In one embodiment, the detection variable determined is a zero-point corrected detection variable, which is the difference between the initial detection variable and a zero point determined during an adjustment (calibration). In this adjustment, the gas detection device is used in an environment where no target gas to be detected is present. Ideally, if no target gas is present, zero is measured as the value for the zero-point corrected detection variable. In particular, due to sensor drift, in practice the zero-point corrected detection variable takes a non-zero value even in the absence of target gas.

It is possible to carry out this adjustment at least once again. In this way, zero drift, in particular due to sensor drift, can be compensated for by calculation up to a certain amount. The invention reduces the number of adjustments required.

The influencing variable estimator may be a part of the evaluation unit. In one embodiment, the gas detection device comprises a housing, and the evaluation unit and the further parts described above are arranged inside this housing. In another embodiment, the evaluation unit and/or the influencing variable estimator are arranged outside this housing. The measured values of the detection variable sensor are transmitted to the evaluation unit and/or to the influencing variable estimator, preferably wirelessly.

The gas detection device according to the invention may be configured as a portable device to be carried by a user. In this embodiment, the gas detection device preferably comprises its own power supply unit. The gas detection device according to the invention may also be configured as a stationary device and be connectable to a stationary power supply network.

In the following, the invention is described by means of embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
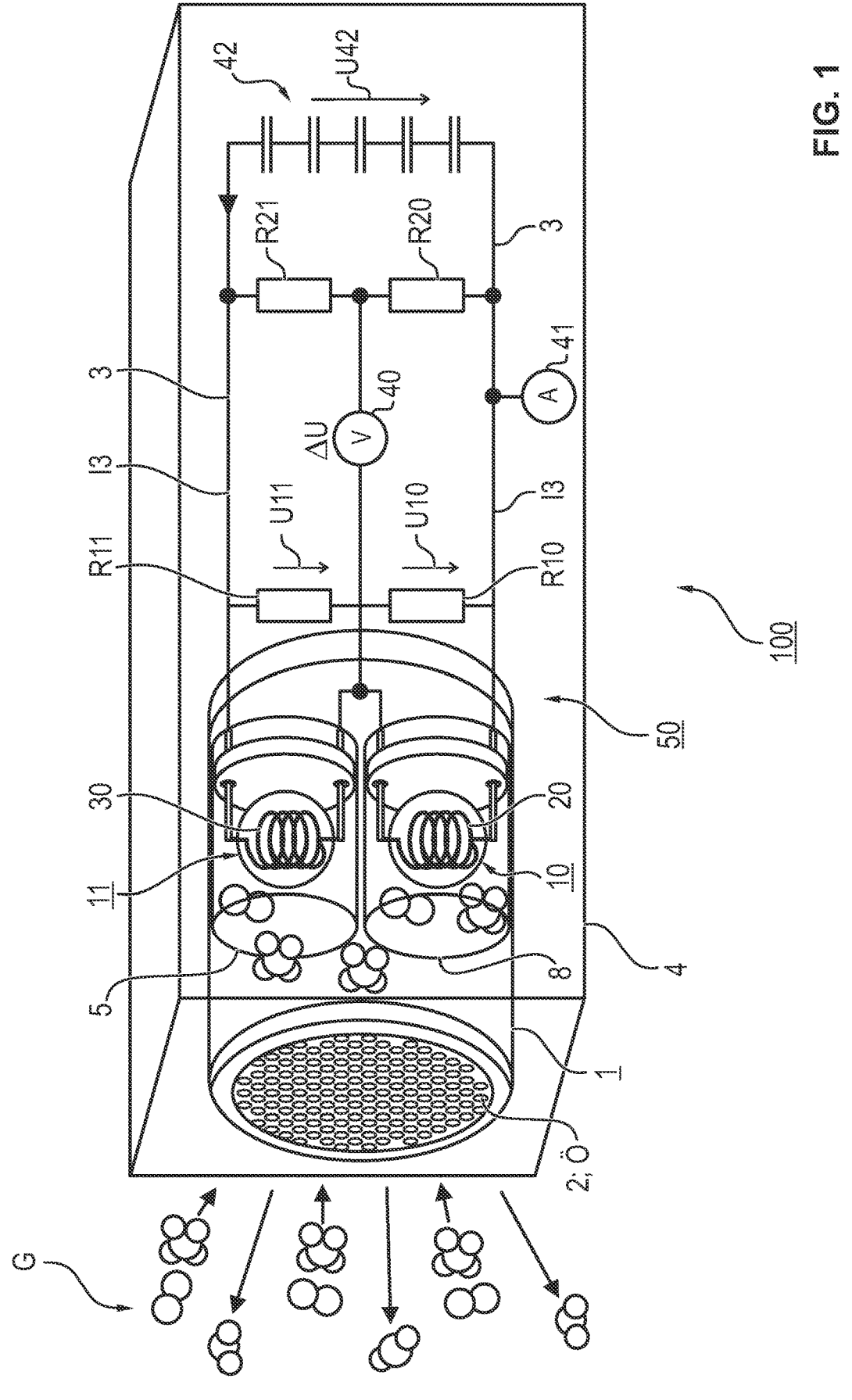
FIG. 1 is a partially schematic perspective view showing an exemplary gas detection device in the form of a heat tone sensor with a detector and a compensator arranged in a Wheatstone measuring bridge.

Referring to the drawings, in the embodiment example, the invention is used for detecting at least one combustible target gas, for example methane ($CH_4$). A gas detection device according to the invention is capable of monitoring a spatial area for the presence of at least one combustible target gas, just like many gas detection devices known in the prior art. In the following, the term "the combustible target gas" is used as an abbreviation, even if several combustible target gases are or may be present in the area.

In one embodiment, the gas detection device measures the concentration of combustible target gas in the area to be monitored and causes an output unit to output information about the measured concentrations in a form that can be perceived by a human. In the case of the presence of multiple combustible target gases, the total (summed) concentration is measured. In another embodiment, the gas detection device automatically checks whether combustible target gas with a concentration above a predetermined concentration threshold is present in the area to be monitored. If a target gas concentration above the concentration threshold is detected, the gas detection device generates an alarm. An output unit outputs this alarm in a form that can be perceived by a human being, for example visually and/or acoustically and/or by a vibration (haptic alarm). In the case of the presence of several combustible target gases, the alarm is generated if the total concentration is above the concentration threshold.

A gas sample flows from the area to be monitored into the interior of the gas detection device and is analyzed there. For example, the gas sample diffuses into the interior or is sucked into the interior by a pump of the gas detection device.

Different operating principles of gas detection devices have become known, for example, the following:

A light source emits electromagnetic radiation that is directed to a photodetector. Preferably, this light source emits infrared radiation. A gas sample to be examined is located in a measuring section between the light source and the photodetector. The photodetector generates an electrical signal depending on the intensity of impinging radiation. Combustible target gas attenuates this electromagnetic radiation. An evaluation unit evaluates the signal from the photodetector and thus measures an indicator for the attenuation.

Electromagnetic radiation causes an acoustic effect inside the gas detection device. Combustible target gas attenuates this acoustic effect. An acoustic sensor, such as a microphone, measures an indicator for this attenuation.

A light source emits electromagnetic radiation, preferably ultraviolet radiation, into a preferably gaseous medium. In the absence of target gas to be detected, the emitted electromagnetic radiation is not sufficient to ionize the medium to any significant extent. The presence of target gas causes more electrical charge carriers to be generated in the form of ions. An indicator for the ionization effected is measured, for example a measure of the current intensity or the amount of ions released.

Combustible target gas is oxidized inside a gas detection device, which device is configured as a so-called heat tone sensor. This principle is used in the embodiment example and explained in more detail below.

The invention can be used in conjunction with any of the principles of action just mentioned.

In all of these cases, the gas detection device includes the core sensor that is acted upon by combustible target gas, particularly in a chemical, electrical, or acoustic manner. A corresponding detection sensor of the gas detection device measures a detection variable, usually an electrical detection variable, which occurs at the core sensor and correlates with the presence and/or concentration of combustible target gas in the measurement chamber and thus in the area to be monitored.

The gas detection device of the embodiment comprises a sensor unit with a sensor configured as a heat tone sensor comprising a detector and a compensator.

An electrical voltage is applied to the detector so that a current flows through an electrically conductive component of the detector. The component heats up and oxidizes combustible target gas in a detector chamber of the sensor unit—of course, only if combustible target gas is present in the area to be monitored. During oxidation, a chemical reaction takes place. This chemical reaction can proceed gradually or lead to burning or even an explosion—the latter is undesirable. An example of combustible target gas is methane ($CH_4$). The following chemical reaction takes place when methane is oxidized:

$$CH_4 + 2O_2 \rightarrow CO_2 + 2H_2O.$$

The oxidation of the combustible target gas releases thermal energy. This thermal energy acts on the electrically conductive component of the detector and changes its electrical resistance. In one implementation, the electrical resistance of the component is greater the higher its temperature is, and in another implementation, the electrical resistance of the component is smaller the higher its temperature is.

A detection variable sensor measures an indicator for the electrical resistance of the component. For example, the electrical voltage applied to the component and the magnitude of the current (amperage) flowing through the component are measured. The electrical resistance correlates to the temperature of the electrically conductive component, and the temperature in turn correlates to the heat energy released during oxidation and therefore to the concentration of combustible target gas in the area being monitored.

In one embodiment, an automatic closed-loop control is performed with the goal of keeping the magnitude of the current (amperage) flowing through the detector component constant. The electrical voltage applied to the component is then proportional to the electrical resistance of the component. In this embodiment, the electrical voltage is a detection variable for the presence and/or concentration of combustible target gas. Accordingly, in another embodiment, automatic closed-loop control is performed with the goal of keeping the applied electrical voltage constant. The current (amperage) then functions as the detection variable.

However, the detection variable, for example the electrical voltage or the current (amperage), is not only influenced by the concentration of combustible target gas, but also by ambient conditions. Therefore, the gas detection device includes a compensator which also has an electrically conductive component. An electric voltage is also applied to the electrically conductive component of the compensator so that the component heats up. A detection variable of the compensator is measured.

In contrast to the detector, however, the compensator is not able to oxidize combustible target gas at all or at least to a lesser extent than the detector. Ambient conditions, on the other hand, influence both the temperature of the electrically conductive component of the detector and the temperature of the electrically conductive component of the compensator, ideally to the same extent. In particular, these ambient conditions include ambient temperature, ambient humidity, and ambient pressure. Ideally, the ambient conditions affect the respective temperature and thus the detection variable of these two components to the same extent. The detection variable of the compensator, for example the electrical voltage applied to the component of the compensator, is subtracted from the detection variable of the detector. Ideally, in the absence of combustible target gas, this difference is zero.

In one embodiment, an electrical voltage is applied continuously to both the detector and the compensator. In another embodiment, the voltage is applied in a pulsed manner so that electrical energy is saved. The pulsed voltage embodiment can be combined with the closed-loop control just described.

FIG. 1 shows an example of the sensor unit 50 of a gas detection device 100, wherein the sensor unit 50 comprises a detector 10 and a compensator 11. The electrically conductive component 20 of the detector 10 and the electrically conductive component 30 of the compensator 11 are both in the form of a spiral wire and are made, for example, of platinum or rhodium or tungsten or an alloy using at least one of these metals. The detector 10 and the compensator 11 are arranged in a so-called Wheatstone measuring bridge. Other electrical circuits are also possible.

The electrical voltage U10 is applied to the detector 10, and the electrical voltage U11 is applied to the compensator 11. A voltage sensor 40, as the detection variable sensor, measures the bridge voltage ΔU. In the embodiment example, this bridge voltage ΔU functions as the initial detection variable that correlates with the concentration of combustible target gas in the area to be monitored.

In FIG. 1, the electrical resistance R10 of the detector 10 and the electrical resistance R11 of the compensator 11 are indicated. An electrical resistor component R20 is connected in parallel with the detector 10, and an electrical resistor component R21 is connected in parallel with the compensator 11. R20 and R21 are used to denote electrical components, and R10 and R11 are used to denote electrical variables (electrical resistance). The electrical resistance of the voltage sensor 40 is high compared to the electrical resistances of the components 10, 11, R20, R21. If the two components R20 and R21 have the same electrical resistance and this is considerably greater than the electrical resistances R10 and R11, then ΔU=(U10–U11)/2 holds.

In the embodiment, the gas detection device 100 is configured as a portable device and includes its own power supply 42, such as a plurality of rechargeable batteries that generate an electrical voltage U42. An array of electrical lines 3 connects the voltage source 42 to the Wheatstone measurement bridge. A current intensity sensor 41 measures the amperage I3 of the current flowing through the line 3.

A detector chamber 8 accommodates the detector 10, a compensator chamber 5 accommodates the compensator 11. The two chambers 5, 8 are surrounded by a stable inner housing 1. Via an opening Ö, the inner housing 1 and thus also the two chambers 5, 8 are at least temporarily in fluid communication with the environment and thus with the spatial area to be monitored. Therefore, a gas sample G from the area to be monitored can pass through the opening Ö to both the detector chamber 8 and the compensator chamber 5.

An optional flame retardant 2 in the opening Ö reduces the risk of flames bursting out of the detector chamber 8. The flame retardant 2 has the form of a metallic grid in the opening Ö, for example.

Figure 2:
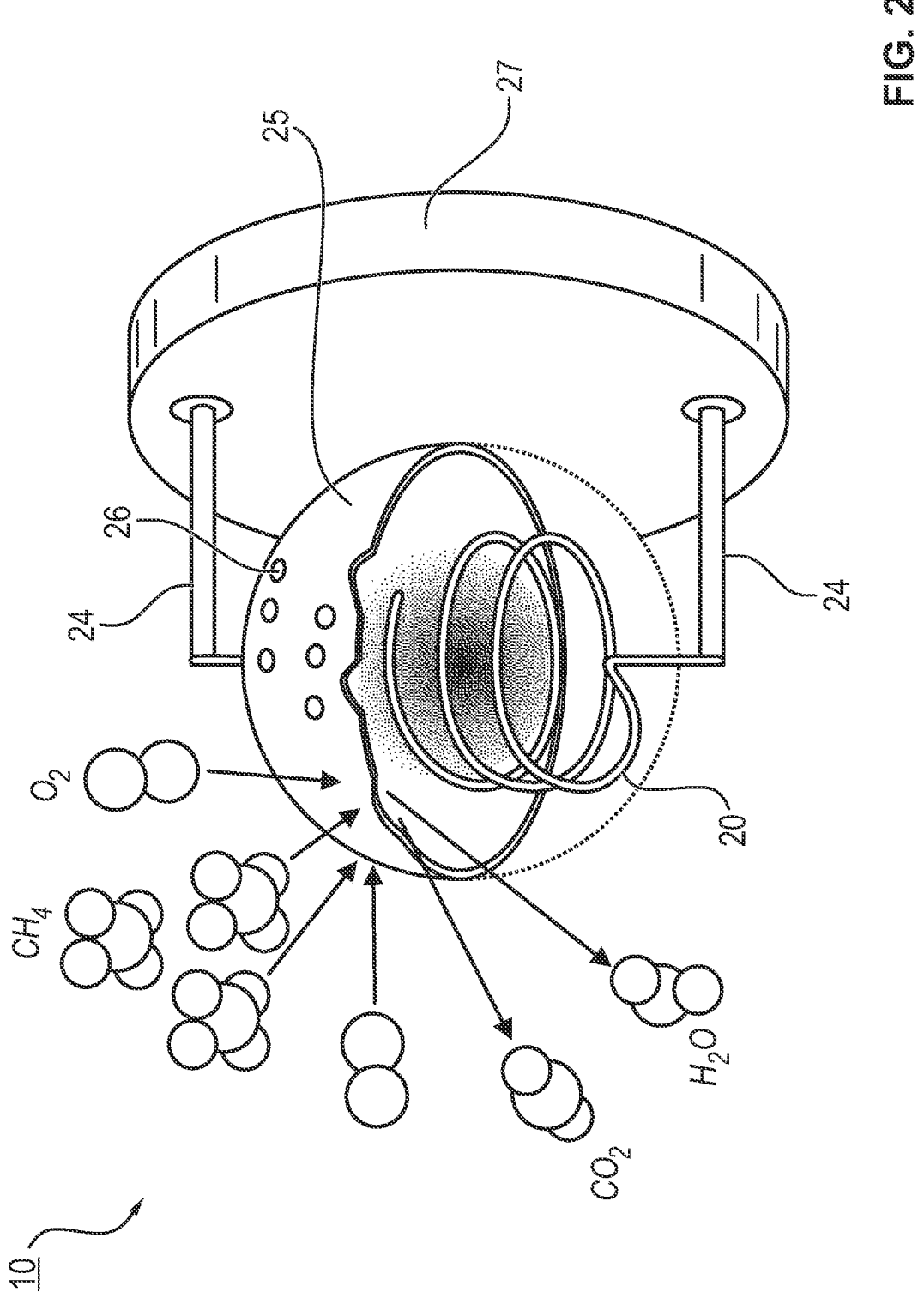
FIG. 2 is a partially schematic perspective view showing an exemplary embodiment of the detector of FIG. 1 as a pellistor.

FIG. 2 shows an exemplary configuration of the detector 10 as a so-called pellistor as well as the oxidation of methane (CH$_4$) as a combustible target gas. The spirally wound electrically conductive wire 20 of the detector 10 is surrounded by a ceramic jacket (ceramic cladding) 25. In the example shown, the ceramic jacket 25 is in the form of a full sphere. The ceramic jacket 25 is thermally conductive and electrically insulating.

A catalytic coating is applied to the outer surface of the ceramic jacket 25, which coating is indicated by circles 26 in FIG. 2. For example, platinum or palladium or another metal or alloy is used as the catalytic material. Alternatively, or in addition to the catalytic coating, catalytic material 26 may also be embedded in the ceramic coating 25. Preferably, the ceramic jacket 25 with the catalytic coating or catalytic material 26 has a porous surface. Thanks to the porous surface, a larger thermally effective area is provided than if the ceramic jacket 25 had a smooth surface.

Two electrical contacts 24 for the wire 20 are shown as examples. A mounting plate 27 holds the full sphere 25, 26.

In the embodiment example, the compensator 11 is also configured as a pellistor and also comprises a spirally wound electrically conductive wire, designated 30 in FIG. 1, as well as a ceramic jacket, electrical contacts and a mounting plate. In contrast to the detector 10, however, the compensator 11 of the embodiment does not have a catalytic coating or other catalytic material 26.

The electrical voltage U10 applied to the detector 10 causes the electrically conductive wire 20 to be heated up to a temperature that is between 400° C. and 550° C. The electrical voltage U11 applied to the compensator 11 causes the electrically conductive wire 30 to also be heated to a temperature between 400° C. and 550° C. However, this temperature alone is not sufficient to oxidize combustible target gas to any appreciable extent. In contrast, the catalytic coating 26 of the detector 10, in conjunction with the high temperature, causes combustible target gas to be oxidized. Because the compensator 11 in the embodiment example does not have a catalytic coating, it is not able to oxidize combustible target gas, or only to a significantly lesser extent.

Preferably, an adjustment (calibration) is made at least prior to the first use of the gas detection device 100. This adjustment is optionally performed again at least once later. During the adjustment or during each adjustment, the gas detection device 100 is deployed in an area that is free of combustible target gas. At least once, the voltage sensor 40 measures the output bridge voltage ΔU in the absence of combustible target gas. Optionally, the voltage sensor 40 measures the output bridge voltage ΔU several times, and an average or median of the measured values is formed. The adjustment provides a so-called zero point Δu$_0$, i.e. a value of the output bridge voltage ΔU in the absence of combustible target gas. Due to configuration differences between the detector 10 and the compensator 11, this zero point Δu$_0$ may differ from zero even before the first use. Because aging can affect the compensator 11 differently than the detector 10, the zero point Δu$_0$ can change over time (zero drift). One way to compensate for this change in zero is to perform an adjustment again.

In the embodiment example, the bridge voltage ΔU$_{korr,0}$ corrected for design-related and optionally for age-related differences is preferably used as the detection variable, i.e. ΔU$_{korr,0}$=ΔU–Δu$_0$=(U10–U11)/2–Δu$_0$.

The detection variable ΔU$_{korr,0}$ is hereinafter referred to as the "zero-point corrected bridge voltage" and is used as the detection variable as defined in the claims.

In one embodiment, the gas detection device 100 automatically detects a target gas in the case that the zero-point corrected bridge voltage ΔU$_{korr,0}$ is outside a predetermined detection tolerance range around zero. In another embodiment, a functional relationship F between the concentration Con of combustible target gas and the zero-point corrected bridge voltage ΔU$_{korr,0}$ is empirically determined prior to initial deployment. To determine this relationship F, the gas detection device 100 is deployed in an environment with a known concentration of combustible target gas, varying this target gas concentration. The respective resulting value ΔU$_{korr,0}$(t) for the zero-point corrected bridge voltage ΔU$_{korr,0}$ at a sampling time t is measured. This results in a sample with several measured value tuples, each measured value tuple comprising a target gas concentration con and a value for the zero-point corrected bridge voltage ΔU$_{korr,0}$. Using the sample, for example by a regression analysis, the empirical relationship $$\Delta U_{korr,0}=F(Con)$$

is determined and stored in a data memory of the gas detection device 100. This relationship F has, for example, the form $$\Delta U_{korr,0}=\alpha*Con.$$

In use, the gas detection device 100 provides a measured value ΔU$_{korr,0}$(t) for the zero-point corrected bridge voltage $\Delta U_{korr,0}$ at a sampling time t. If no influencing variable acts on the zero-point corrected bridge voltage $\Delta U_{korr,0}$, the sought concentration (con) can be determined at least approximately according to the calculation rule $$con=F^{-1}[\Delta U_{korr,0}(t)].$$

Both the detector 10 and the compensator 11 age over time. Frequently, these two components 10, 11 age at different rates. The following influences in particular contribute to the different aging:

The high temperature of the components 20 and 30 causes the ceramic coatings 25 to sinter. Because the detector 10 has catalytic material 26, but the compensator 11 has no catalytic material at all or at least less, the detector 10 often sinters faster than the compensator 11. This is especially true when the detector 10 has a porous surface and the compensator 11 does not.

Both the detector 10 and the compensator 11 age thermally. This is due to the fact that the detector 10 reaches a higher temperature than the compensator 11 in the presence of combustible target gas because of the ceramic material 26.

Harmful gases, for example siloxanes or hydrogen sulfides, are reacted at the detector 10 due to the catalytic material 26. This leads to deposits on the surface of the ceramic coating 25. On the surface of the compensator 11, this effect occurs only to a lesser extent or even not at all.

In many cases, the different processes involved in aging the detector 10 and aging the compensator 11 cause the detection variable, in this case the zero-point corrected bridge voltage $\Delta U_{korr,0}=\Delta U-\Delta u_0$, to be outside the detection tolerance range mentioned above around zero even when no combustible target gas is present. In one embodiment, the zero-point corrected bridge voltage $\Delta U_{korr,0}$ drifts and increases or decreases over time, even when no combustible target gas is present. Thanks to the invention, the adjustment described above needs to be performed less frequently in many cases than with known gas detection devices.

Figure 3:
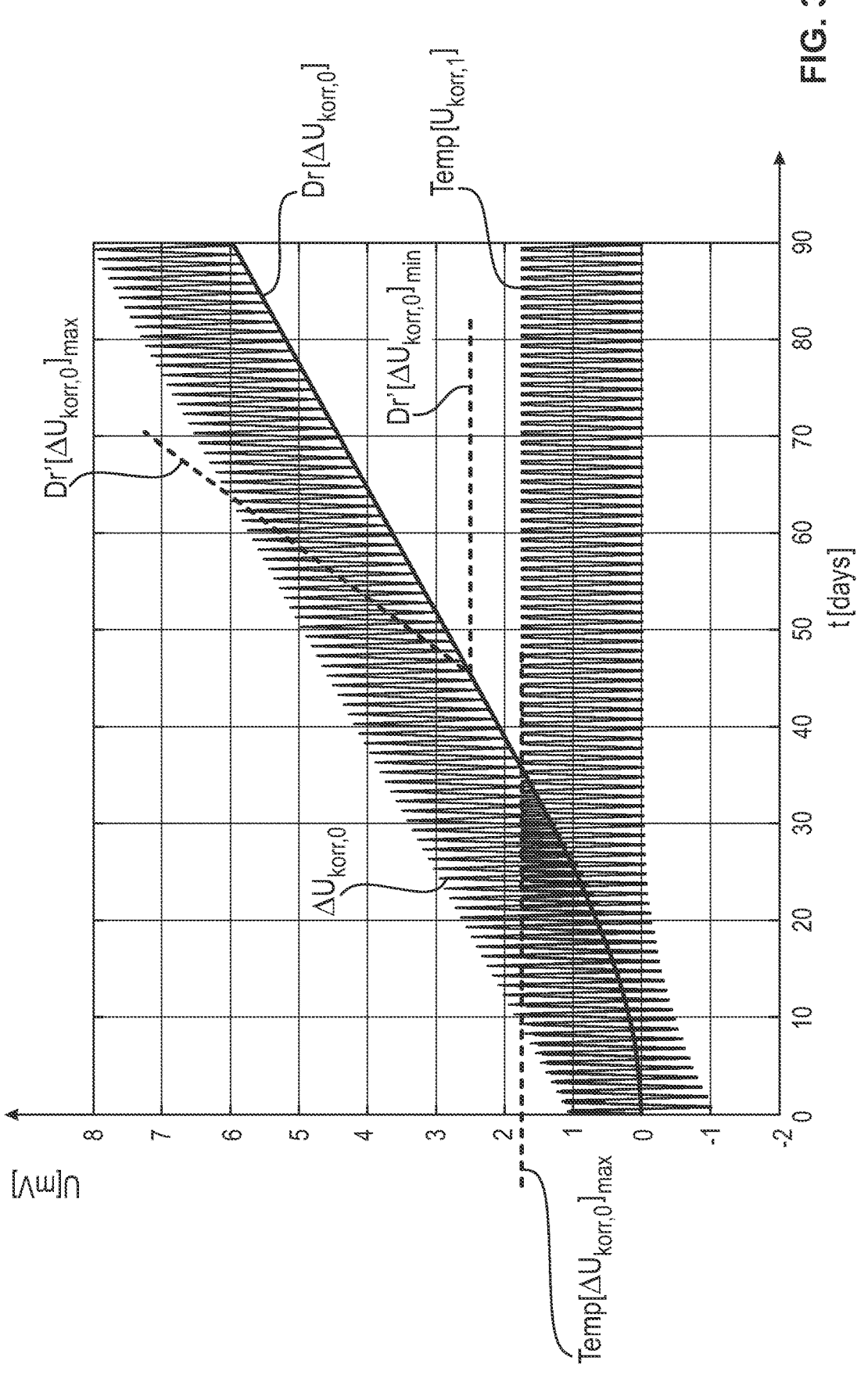
FIG. 3 is a graph showing a first example with a time course of the zero-point corrected bridge voltage of the device of FIG. 1, an estimated time course of the influence of drift and an estimated time course of the influence of daily temperature variation.
Figure 4:
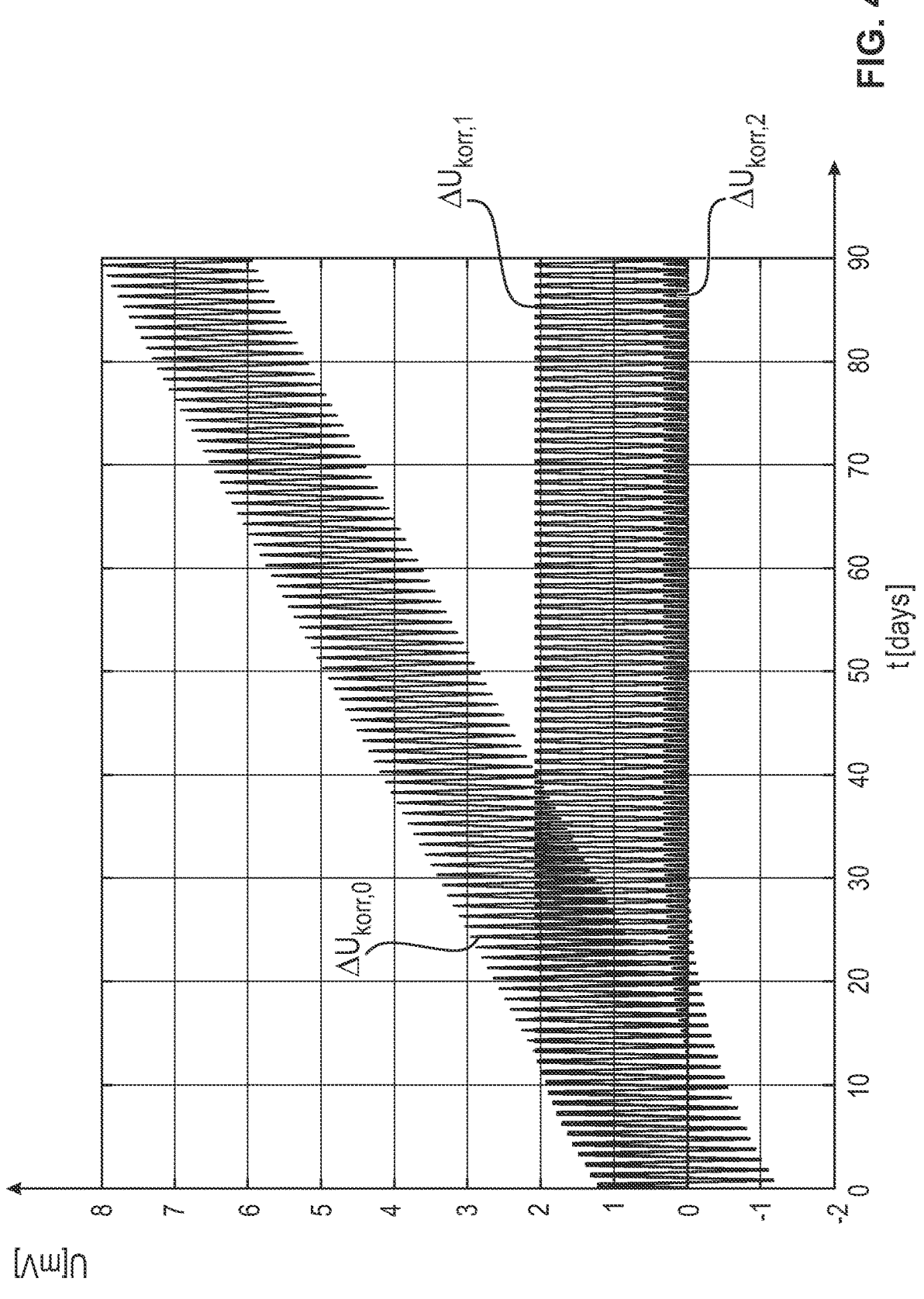
FIG. 4 is a graph showing an exemplary course of the zero-point corrected bridge voltage of FIG. 3 as well as a time course of the zero-point corrected bridge voltage adjusted for drift and temperature influence.
Figure 5:
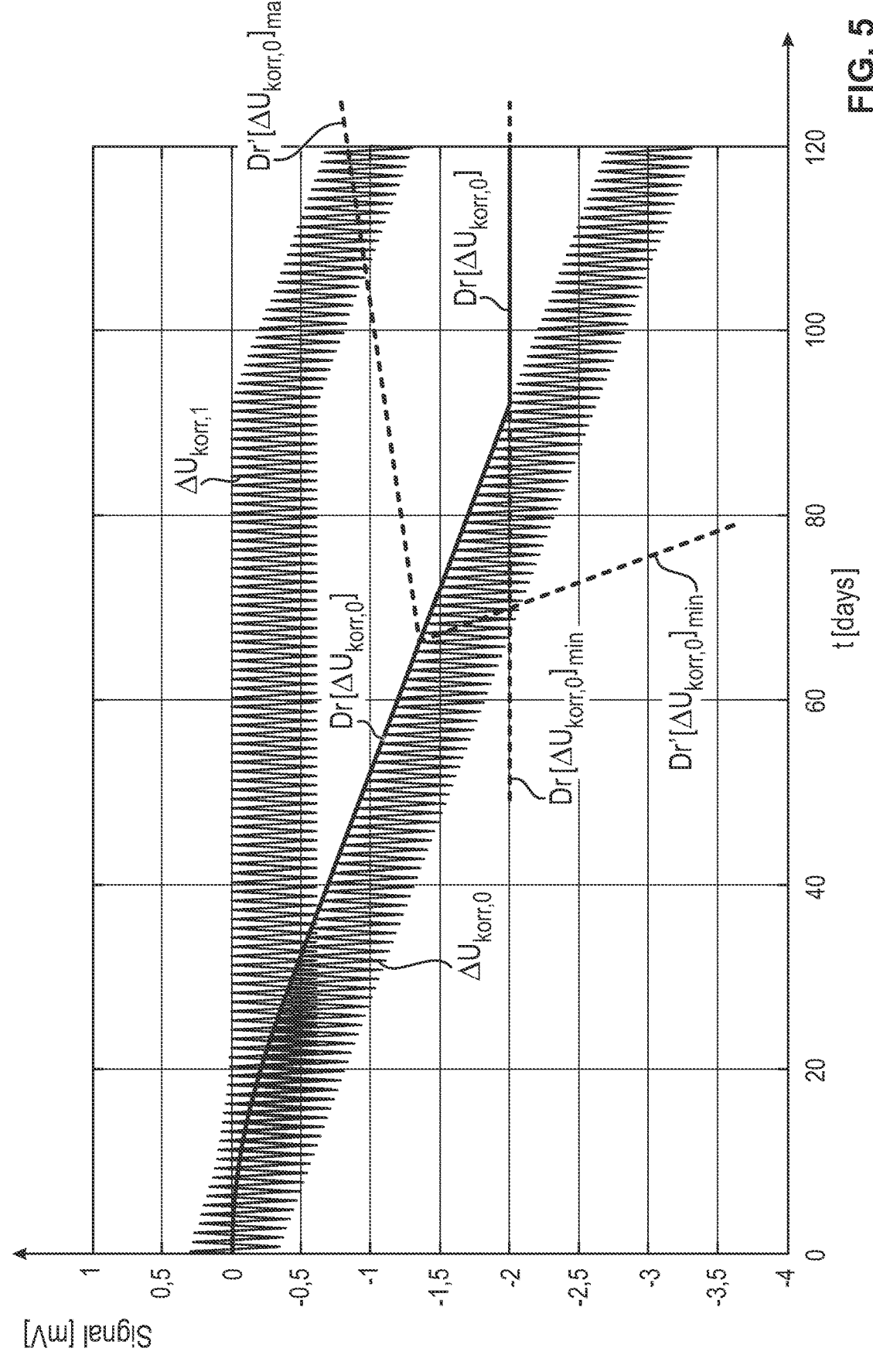
FIG. 5 is a graph showing a second example with a time course of the zero-point corrected bridge voltage, an estimated time course of drift, and a time course of the zero-point corrected bridge voltage adjusted for drift.
Figure 6:
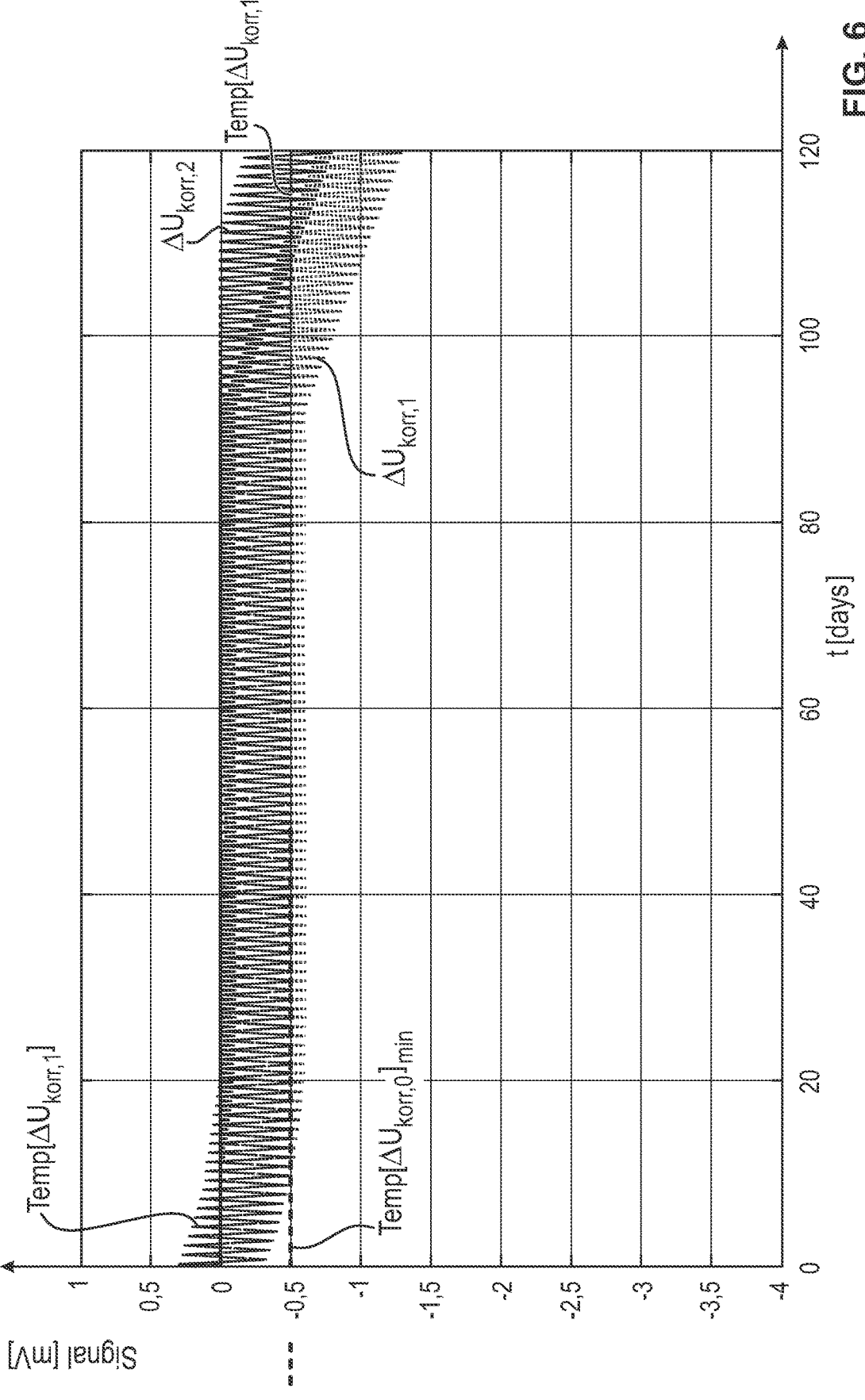
FIG. 6 is a graph showing a time course of FIG. 5 of the zero-point corrected bridge voltage adjusted for drift, as well as an estimated time course of the influence of daily temperature variation and a time course of the zero-point corrected bridge voltage adjusted for drift and temperature influence.
Figure 7:
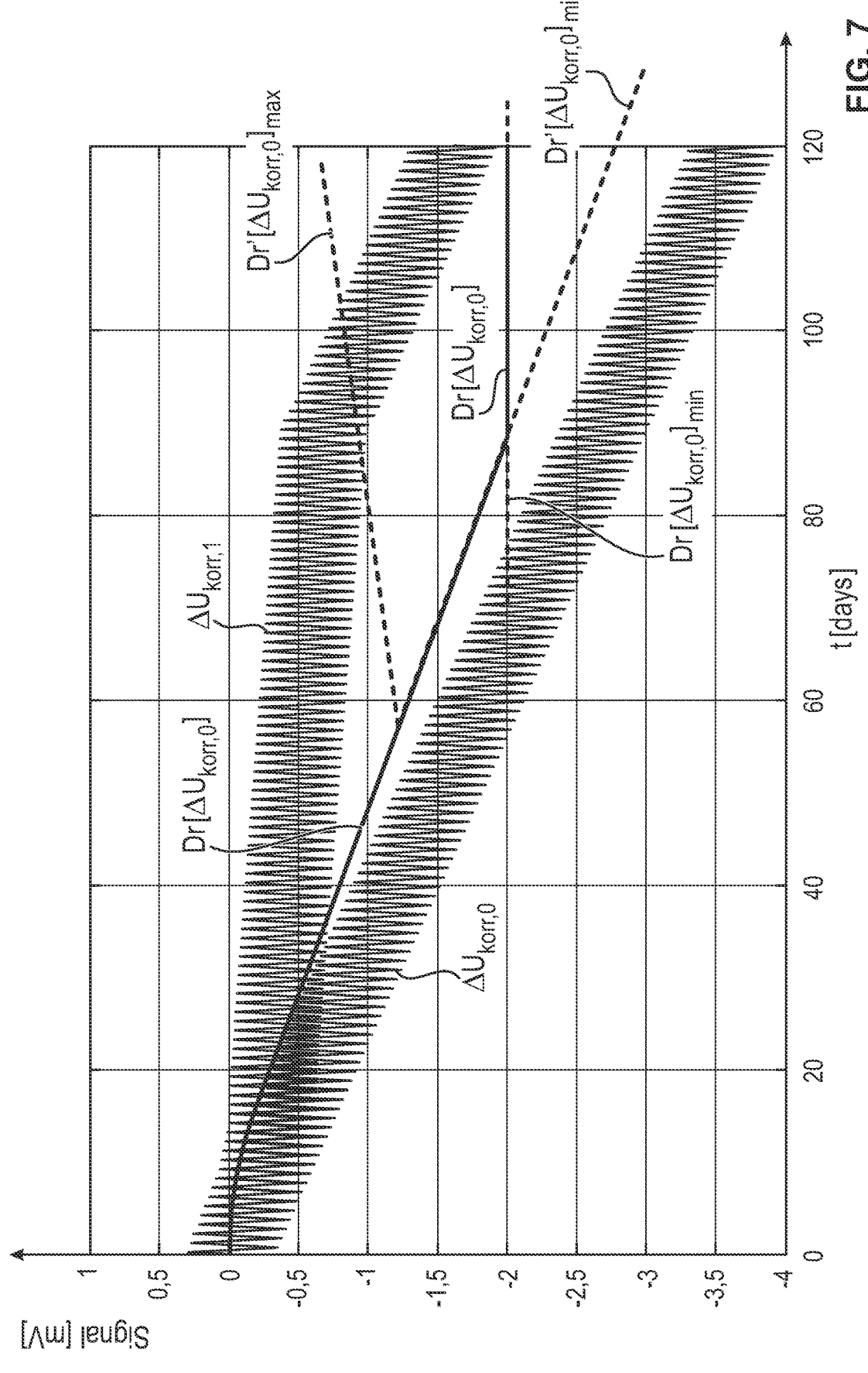
FIG. 7 is a graph showing a third example with a time course of the zero-point corrected bridge voltage, an estimated time course of drift, and a time course of the zero-point corrected bridge voltage adjusted for drift.

FIG. 3, FIG. 5, and FIG. 7 each show an exemplary drift, where no adjustment was performed in the time periods shown and the detection variable, i.e. the zero-point corrected bridge voltage $\Delta U_{korr,0}$ becomes increasingly larger (FIG. 3) or increasingly smaller (FIG. 5, FIG. 7). On the x-axis from FIG. 3 to FIG. 8 the time in days is plotted, on the y-axis the detection variable in mV. The representations of the time courses are schematic representations and not necessarily true to scale.

In the embodiment shown, the temperatures of the detector 10 and the compensator 11 also depend on the ambient temperature. Often, the detector 10 reacts differently to the ambient temperature than the compensator 11. Therefore, the detection variable, in this case the zero-point corrected bridge voltage $\Delta U_{korr,0}$, also depends on the ambient temperature.

As is well known, the ambient temperature is significantly influenced by the time of day (dAy): It is usually colder at night than during the day. Therefore, the periodically fluctuating ambient temperature leads to an oscillating detection variable. This oscillation is exemplarily shown in FIG. 3, FIG. 6, and FIG. 8.

Another factor influencing the ambient temperature can be a weather change and/or the season, which can cause the ambient temperature to change within a few hours or days, often by more than 10° C. In addition, a weather change and the time of year can cause the ambient pressure and/or humidity to change.

In addition, the gas detection device 100 often does not continuously monitor the area for days or even weeks, but is turned off in between, particularly to save electrical energy. If the gas detection device 100 is switched off after an operation and switched on again after a rest period, it must warm up. Also, during this warm-up period, the gas detection device 100 is able to measure the detection variable. Even if no combustible target gas is present, the detection variable may take on different values during the warm-up phase than after the warm-up phase is complete.

In the preceding paragraphs, four different influencing variables were described as examples, each of which has an influence on the detection variable, i.e. in this case on the zero-point corrected bridge voltage $\Delta U_{korr,0}$. The influence of an influencing variable does not usually depend on the presence or absence of combustible target gas. Furthermore, the influence that one influencing variable takes is ideally independent of the influence that another influencing variable takes. Each of these four influencing variables by itself, as well as a superposition of multiple influencing variables, can cause measured values of the detection variable to fall outside the detection tolerance band, even if no combustible target gas is present. It is also possible that values of the detection variable lie within the detection tolerance band even though combustible target gas is present. However, the latter situation is largely avoided.

Aging acts as the slower influencing variable within the meaning of the patent claims. According to the invention, the influence of aging as well as the influence of at least one further influencing variable is therefore compensated for at least approximately by calculation. In order to compensate the influence of an influencing variable approximately by calculation, a time course of the influence of this influencing variable on the original detection variable or on a detection variable in which the influence of another influencing variable is already compensated by calculation is estimated. To estimate the time course, a measurement value series is used. This measurement value series originates from the detection variable, in this case the zero-point corrected bridge voltage $\Delta U_{korr,0}$, or from the detection variable after the influence of another influencing variable has already been compensated for by calculation. This feature eliminates the need to measure the influence of the influencing variable directly. For example it is possible but, thanks to this feature, not necessary to directly measure the ambient temperature or a temperature inside the gas detection device 100.

According to a preferred embodiment of the invention, a step-by-step procedure is carried out with one step for each influencing variable whose influence is to be compensated computationally.

In the first step, the influence of a selected influencing variable is compensated by calculation. A time sequence of values of the detection variable, in this case the zero-point corrected bridge voltage $\Delta U_{korr,0}$, is used as a measurement value series. Using this measurement value series, the time course of the influence of the selected influencing variable on the detection variable is estimated. The estimated time course of the influence is then subtracted from the detection variable. In this way, a corrected detection variable is generated in the first step, namely a detection variable in which the influence of the selected influencing variable is at least approximately compensated computationally. If, for example, aging is used as the first selected influencing variable, a detection variable is generated in the first step in which the influence of aging on the original detection variable is at least approximately compensated computationally.

In the or each further step, the influence of a further selected influencing variable is compensated by calculation. The values of the corrected detection variable in which the influence of the or each previously selected influencing variable was compensated by calculation are used as the measurement value series. Using this measurement value series, the time course of the influence of the further selected influencing variable on the corrected detection variable generated in the previous step is compensated by calculation. The further step provides a further corrected detection variable, namely a detection variable in which additionally the influence of the further selected influencing variable is compensated.

Preferably, the same algorithm is used in each step to estimate the influence of an influencing variable and then compensate for it. Preferably, the steps to compensate for the influence of the influencing variables are performed again for each sampling time.

The invention exploits or presupposes the fact that the influencing variables act independently of each other on the detection variable. The influence of an influencing variable on the original detection variable is therefore ideally equal to the influence of this influencing variable on a corrected detection variable, i.e. on a detection variable in which the influence of at least one other influencing variable has already been compensated for by calculation. Therefore, different sequences are possible in which the respective influence of the influencing variables is compensated computationally.

Note: A similar effect on the detection variable can have different causes. For example, a variable ambient temperature can be caused by the time of day, by the season of the year, or by a change in the weather. If these different causes lead to different change tolerance bands, they are treated as different influencing variables, otherwise they are combined into one influencing variable.

In the embodiment described below, the influence of the slower influencing variable, namely the influence of aging, on the detection variable, in the embodiment on the zero-point corrected bridge voltage $\Delta U_{korr,0}$, is compensated for by calculation in the first step. The influence of aging on the detection variable is subsequently referred to as the "drift" of the detection variable. In the second step, the influence of a second influencing variable on the compensated detection variable generated in the first step is compensated computationally.

In the embodiment example, the zero-point corrected bridge voltage adjusted for the influence of drift is generated as the corrected detection variable in the first step. This corrected detection variable is denoted by $\Delta U_{korr,1}$. The influence of the ambient temperature due to the time of day is used as a faster influencing variable. It is well known that the ambient temperature varies during the day depending on the time of day. The second step provides a twofold corrected detection variable, namely the zero-point corrected bridge voltage adjusted for the estimated influence of aging and of the time-of-day dependent temperature variation. This twofold corrected detection variable is denoted by $\Delta U_{korr,2}$.

Each influencing variable causes the values of the detection variable to change even in the absence of combustible target gas. The maximum possible change per time unit of the detection variable caused by the influence of an influencing variable, i.e. the variability, usually differs from influencing variable to influencing variable. The influencing variables can be put into a variability order in such a way that in the variability order the maximum possible change per time unit of the detection variable due to the influencing variable increases. For the example described above, the variability order is, for example, the following:

first influencing variable (lowest variability, slowest influencing variable): Aging of the gas detection device 100, second influencing variable: season, which usually changes the ambient temperature, third influencing variable: change of ambient temperature and/or absolute or relative humidity due to the time of day—this influencing variable is ideally periodic with a period duration of one day, fourth influencing variable (highest variability, fastest influencing variable): Change of the detection variable during a warm-up phase after the gas detection device 100 is switched on.

In general, intrinsic influencing factors, in particular aging, occur first (smallest variability) in the variability sequence, then external influencing factors, in particular ambient temperature and humidity, and finally (highest variability) dynamic factors, in particular due to switching on the gas detection device.

Preferably, the respective influence of these four or some of these four influencing variables is compensated computationally according to the variability order, i.e. first the influencing variable with the lowest variability. As already mentioned, however, a different order is also possible for the computational compensation.

As already described, for at least two influencing variables a time course of the influence of this influencing variable on the detection variable is estimated. Subsequently, this estimated influence is compensated computationally by subtracting the estimated time course from the detection variable or from an already corrected detection variable. The time course of an influencing variable is estimated using a measurement value series. This measurement value series is derived from the measured values of the detection variable or of the corrected detection variable, i.e. without using a sensor for the influencing variable. The measurement value series used may therefore comprise measurement values of the detection variable or a corrected detection variable, which were measured in the presence of a combustible target gas. The influence of the influencing variables on the detection variable is to be distinguished from the effect of combustible target gas. It is to be prevented that the computational compensation leads to the fact that a combustible target gas is not detected. The possibility is accepted that sometimes a false alarm is generated because the influence of an influencing variable has not been fully compensated and the remaining influence can therefore simulate the presence of combustible target gas.

To distinguish the influence of an influencing variable from the effect of combustible target gas, a change tolerance band is predefined for each influencing variable. This change tolerance band defines the thresholds within which the estimated time course of the influence of the influencing variable can change per time unit if no combustible target gas is present. In the step of estimating the time course of the influence of the influencing variable, the lower threshold and the upper threshold of the change tolerance band for this influencing variable are considered as boundary conditions.

The two thresholds of the change tolerance band are specified, for example, depending on how much the detection variable can change at most per time unit due to the actual influence of the influencing variable. It is also possible that the two thresholds are specified depending on regulatory requirements. Such regulatory requirements can limit a computational compensation of a detection variable in order to ensure that the or at least one specified target gas is actually detected with sufficiently high reliability.

Further above a variability order among the influencing variables was described. The change tolerance bands are preferably determined depending on this variability sequence in such a way that the following effect is achieved: The change tolerance band of an influencing variable is completely contained in the change tolerance band of the following influencing variable in the variability order and is narrower (smaller distance between the two thresholds) than the change tolerance band of the following influencing variable.

In the example described below, aging is used as the first and slower influencing variable, which causes a drift of the detection variable (zero-point corrected bridge voltage $\Delta U_{korr,0}$) As a second and at the same time as a faster influencing variable the temperature variation dependent on the time of day is used. A narrower change tolerance band, which applies to the slower influencing variable, and a wider change tolerance band, which applies to the faster influencing variable, are specified.

As explained earlier, the estimated time course of the drift is denoted by $Dr[\Delta, U_{korr,0}]$. The lower bound of the narrower change tolerance band is denoted by $Dr'[\Delta U_{korr,0}]_{min}$, and the upper bound is denoted by $Dr'[\Delta U_{korr,0}]_{max}$. Thus, the narrower change tolerance band is the interval from $Dr'[\Delta U_{korr,0}]_{min}$ to $Dr'[\Delta U_{korr,0}]_{max}$.

The time course of the influence of the faster influencing variable is estimated by using a measurement value series of the detection variable adjusted for the estimated influence of the slower influencing variable (drift). This detection variable adjusted for the estimated influence of the slower influencing variable is denoted $\Delta U_{korr,1}$. The lower bound of the wider change tolerance band is denoted $Temp'[\Delta U_{korr,0}]_{min}$, and the upper bound is denoted $Temp'[\Delta U_{korr,0}]_{max}$.

In one embodiment, a total (entire) change tolerance band is predefined. This total change tolerance band defines the thresholds within which the estimated time courses of the summed influences of all influencing variables can at most change per time unit. This overall change tolerance band is preferably set such that a gradual increase in a concentration of at least one target gas that is above a predetermined rate of increase can be reliably distinguished from a change in the detection variable due to the influence of the influencing variables. The sum of the lower thresholds of each change tolerance band is equal to the lower threshold $Ein'_{min}$ of the total change tolerance band, and the sum of the upper thresholds is equal to the upper threshold $Ein'_{max}$ of the total change tolerance band. When setting the change tolerance bands for the influencing variables, the boundary condition that the boundary condition just described is met is taken into account.

In the embodiment example, in addition to the change per time unit, the value of a computational compensation is limited upwards and downwards, i.e. a value range per influencing variable for the respective influence of every considered influencing variable is predefined. This has the effect that in the step of compensating the entire influence of the influencing variables by calculation, the detection variable is changed by the compensation only within an overall value range. In this way, the risk of the following undesirable effect occurring is reduced: due to excessive compensation, a defect or severe aging of the gas detection device 100 is not detected. This, in turn, could result in the gas detection device 100 failing to detect a combustible target gas. The lower threshold of the total value range is denoted as $Ein_{min}$, and the upper threshold is denoted as $Ein_{max}$.

For the second and each further influencing variable according to the variability sequence, a respective value range is defined. In one embodiment, a value range is also specified for the slower influencing variable, namely a wider value range. The time course of the influence of an influencing variable on the detection variable is estimated in such a way that each value of this time course lies within the predetermined value range for the influence of the influencing variable. The value range of an influencing variable is wider than the value range of the subsequent influencing variable in the variability sequence and includes the value range of the subsequent influencing variable.

In the embodiment example, the upper threshold of the wider value range, i.e. the value range for the drift, which is the estimated influence of the first influencing variable (aging) on the zero-point corrected bridge voltage $\Delta U_{korr,0}$, is denoted by $Dr[\Delta U_{korr,0}]_{max}$, and the lower threshold by $Dr[\Delta U_{korr,0}]_{min}$. The upper threshold of the narrower value range, which is the value range for the estimated influence of the time-of-day dependent temperature changes (faster influencing variable), is denoted $Temp[\Delta U_{korr,0}]_{max}$, and the lower threshold is denoted $Temp[\Delta U_{korr,0}]_{min}$.

The following two boundary conditions are observed when defining the value ranges:

The sum of the lower thresholds of the individual value ranges is equal to the lower threshold $Ein_{min}$ of the total value range.

The sum of the upper thresholds of the individual value ranges is equal to the upper threshold $Ein_{max}$ of the total value range.

Given is a sequence of sampling times (time points) $t_0$, $t_1$, $t_2$, . . . . In one implementation, the sampling times $t_0$, $t_1$, $t_2$, . . . are arranged equidistantly, so that the sequence has the form $t_0$, $t+\Delta t$, $t_0+2*\Delta t$, $t_0+3*\Delta t$, . . . . The sampling times $t_0$, $t_1$, $t_2$, . . . can also be unevenly distributed along the time axis.

The detection variable, in this case the zero-point corrected bridge voltage $\Delta U_{korr,0}$, is measured at least at each sampling time $t_i$. Thus, a measurement value series $\Delta U_{korr,0}(t_0)$, $\Delta U_{korr,0}(t_1)$, $\Delta U_{korr,0}(t_2)$, $\Delta U_{korr,0}(t_3)$, . . . is obtained.

In a preferred embodiment, the influence of the drift $Dr[\Delta U_{korr,0}]$ is compensated computationally by a subtraction, i.e.

$$\Delta U_{korr,1}=\Delta U_{korr,0}-Dr[\Delta U_{korr,0}], \text{ and therefore} \tag{1}$$

$$\Delta U_{korr,1}(t_i)=\Delta U_{korr,0}(t_i)-Dr[\Delta U_{korr,0}](t_i) \quad (i=0,1, \atop 2,\ldots). \tag{2}$$

Subsequently, the influence of the faster influencing variable is computationally compensated for by subtracting it from the detection variable $\Delta U_{korr,1}$ already adjusted for drift. This yields the detection variable $\Delta U_{korr,2}$. The calculation rule is thus $$\Delta U_{korr,2}=\Delta U_{korr,1}-Temp[\Delta U_{korr,1}], \text{ i.e.} \tag{3}$$

$$\Delta U_{korr,2}(t)=\Delta U_{korr,1}(t_i)-Temp[\Delta U_{korr,1}](t_i). \tag{4}$$

Preferably, these steps are performed again for each sampling time $t_i$. This provides a measured value $\Delta U_{korr,2}(t_i)$ for each sampling time $t_i$.

In one embodiment, the presence of combustible target gas at a sampling time $t_i$ is detected if the measured value $\Delta U_{korr,2}(t_i)$ for this sampling time $t_i$ is outside a predetermined detection tolerance band around zero. In another embodiment, an estimated value con is derived for the target gas concentration Con at the sampling time $t_i$. Further above, it was described how a relationship F between the target gas concentration Con and the resulting zero-point corrected bridge voltage $\Delta U_{korr,0}$ was empirically determined. Preferably, this relationship F is also used for the corrected detection variable $\Delta U_{korr,2}$. A value con for the concentration Con is derived according to the calculation rule con=$F^{-1}$ [$\Delta U_{korr,2}(t_i)$].

The two embodiments can be combined as follows: On the one hand, the gas detection device 100 generates an alarm when the measured value $\Delta U_{korr,2}(t_i)$ is outside the predetermined detection tolerance band, and on the other hand it determines the target gas concentration con=$F^{-1}$ [$\Delta U_{korr,2}(t_i)$]. The alarm and/or the determined target gas concentration are preferably output in a form that can be perceived by a human, namely by an output unit of the gas detection device 100 itself and/or by a spatially remote receiver.

According to the embodiment example just described, measured values of the zero-point corrected detection variable $\Delta U_{korr,0}$ are used to estimate the respective time course of the influence of an influencing variable and, in particular, to generate the two estimated time courses $Dr[\Delta U_{korr,0}]$ and $Temp[\Delta U_{korr,1}]$.

In a preferred embodiment, the measured value $\Delta U_{korr,0}$ $(t_i)$ of the zero-point corrected detection variable $\Delta U_{korr,0}$ at the sampling time $t_i$ is used to estimate the time course of the influence of an influencing variable only if the following condition is fulfilled at the sampling time $t_i$: The measured value $\Delta U_{korr,2}(t_i)$ of the detection variable $\Delta U_{korr,2}$ adjusted for the influence of (all) influencing variables lies within the detection tolerance band mentioned above, i.e., no combustible target gas outside the detection limit is present. If, on the other hand, the measured value $\Delta U_{korr,2}(t_i)$ lies outside this detection tolerance band, the measured value $\Delta U_{korr,0}(t_i)$ is not used to estimate the time histories. This is because combustible target gas is detected during such a time period. This preferred embodiment reduces the risk that the presence of combustible target gas will bias the estimate of the contribution of drift and/or the estimate of the contribution of ambient temperature. Rather, an interpolation or extrapolation is preferably performed for a period of time with target gas, using measured values taken at a condition free of combustible target gas. It is also possible to reuse a measured value taken in the absence of combustible target gas for several subsequent sampling times.

In one implementation, the overall variability tolerance band described above and/or the overall value range described above are additionally or instead used to automatically decide whether or not to use a measured value $\Delta U_{korr,0}$ $(t_j)$ of the detection variable $\Delta U_{korr,0}$ for a sampling time $t_j$ to estimate the respective time course of the influencing variable. The overall variability tolerance band ranges from $Ein'_{min}$ to $Ein'_{max}$. The total value range is from $Ein_{min}$ to $Ein_{max}$. The starting point is a sampling time $t_i$, at which no combustible target gas is present, which is detected, for example, by the measured value $\Delta U_{korr,2}(t_i)$ being within the detection tolerance band just described. For a subsequent sampling time $t_{i+m}$, it is checked whether at least one of the following two conditions is fulfilled or not:

$$Ein'_{min}*(t_{i+m}-t_i)<=\Delta U_{korr,0}(t_{i+m})-\Delta U_{korr,0}(t_j)$$
$$<=Ein'_{max}*(t_{i+m}-t_i) \text{ and/or} \tag{5}$$

$$Ein_{min}<=\Delta U_{korr,0}(t_{i+m})-\Delta U_{korr,0}(t_j)<=Ein_{max} \tag{6}$$

Only if condition (5) is fulfilled, the change of the detection variable $\Delta U_{korr,0}$ between the two sampling times $t_{i+m}$ and $t_i$ can be attributed to the influencing variables, otherwise combustible target gas contributes to the change.

Only when condition (6) is satisfied, the difference in the detection variable $\Delta U_{korr,0}$ between the two sampling times $t_{i+m}$ and $t_i$ can be attributed to the influencing variables.

In the following, different implementations are described as to how the time course of the influence of an influencing variable is estimated. First, it is described how the time course of the slower influencing variable, i.e. the time course of the drift, is estimated. As already explained, the estimated time course is denoted by $Dr[\Delta U_{korr,0}]$.

In one implementation, the time course $Dr[\Delta U_{korr,0}]$ of the drift is estimated by a recursive calculation. The starting point is a sampling time to, where no combustible target gas is present and where the value of the drift for this sampling time to is known. For example, an adjustment was completed at the sampling time to, and therefore $Dr[\Delta U_{korr,0}]$ $(t_0)=0$.

Then the following recursion formula is used:

$$Dr[\Delta U_{korr,0}](t_i)=Dr[\Delta U_{korr,0}](t_{i-1})+\Delta 1(i)(i=1,2,3,\ldots). \tag{7}$$

Here $$\Delta 1(i)=\Delta U_{korr,0}(t_i)-\Delta U_{korr,0}(t_{i-1}), \text{ if}$$

$$Dr'[\Delta U_{korr,0}]_{min}*(t_i-t_{i-1})<=\Delta U_{korr,0}(t_{i-1})-\Delta U_{korr,0}(t_{i-1})$$

$$<=Dr'[\Delta U_{korr,0}]_{max}*(t_i-t_{i-1}), \tag{8}$$

$$\Delta 1(i)=Dr'[\Delta U_{korr,0}]_{min}*(t_i-t_{i-1}), \text{ if}$$

$$\Delta U_{korr,0}(L)-\Delta U_{korr,0}(t_{i-1})<Dr'[\Delta U_{korr,0}]_{min}*(t_i-t_{i-1}), \text{ and} \tag{9}$$

$$\Delta 1(i)=Dr'[\Delta U_{korr,0}]_{max}*(t_i-t_{i-1}), \text{ if}$$

$$Dr'[\Delta U_{korr,0}]_{max}*(t_i-t_{i-1})<\Delta U_{korr,0}(t_i)-\Delta U_{korr,0}(t_{i-1}) \tag{10}$$

In addition, the drift value range is considered, i.e., each value $Dr[\Delta U_{korr,0}](t_i)$ is determined such that the following applies:

$$Dr[\Delta U_{korr,0}]_{min}<=Dr[\Delta U_{korr,0}](t_i)<=Dr[\Delta U_{korr,0}]_{max} \tag{11}$$

In a corresponding way, the time course of the faster influencing variable, in this case the temperature depending on the time of day, is estimated. Again, the starting point is that for a sampling time to the value of the influence of the faster influencing variable $Temp[\Delta U_{korr,1}]$ is known. The time course of the influence of the faster influencing variable is estimated using a measurement value series of the zero-point corrected bridge voltage adjusted for drift, i.e. using $\Delta U_{korr,1}$.

The wider change tolerance band is taken into account, i.e. the following applies:

$$Temp'[\Delta U_{korr,0}]_{min}*(t_i-t_{i-1})<=[Temp[\Delta U_{korr,1}](t_i)-Temp[\Delta U_{korr,1}](t_{i-1})]$$

$$<=Temp'[\Delta U_{korr,0}]_{max}*(t_i-t_{i-1}) \tag{12}$$

In addition, a given value range for the faster influencing variable is considered, i.e., each value $Temp[\Delta U_{korr,1}](t_i)$ is determined such that the following applies:

$$Temp[\Delta U_{korr,0}]_{min}<=Temp[\Delta U_{korr,1}](t_i)<=Temp[\Delta U_{korr,0}]_{max} \tag{13}$$

It was explained further above that preferably during the period of use the gas detection device 100 is readjusted at least once. After each adjustment, a zero point $\Delta u_0$ for the bridge voltage $\Delta U$ as well as initial values for the respective influence of each considered influencing variable are known, i.e. values for $Dr[\Delta U_{korr,0}]$ and $Temp[\Delta U_{korr,1}]$, which refer to a sampling time to. Preferably, the gas detection device 100 is reset after each adjustment, and the value zero is used as the initial value for an influence.

Figure 8:
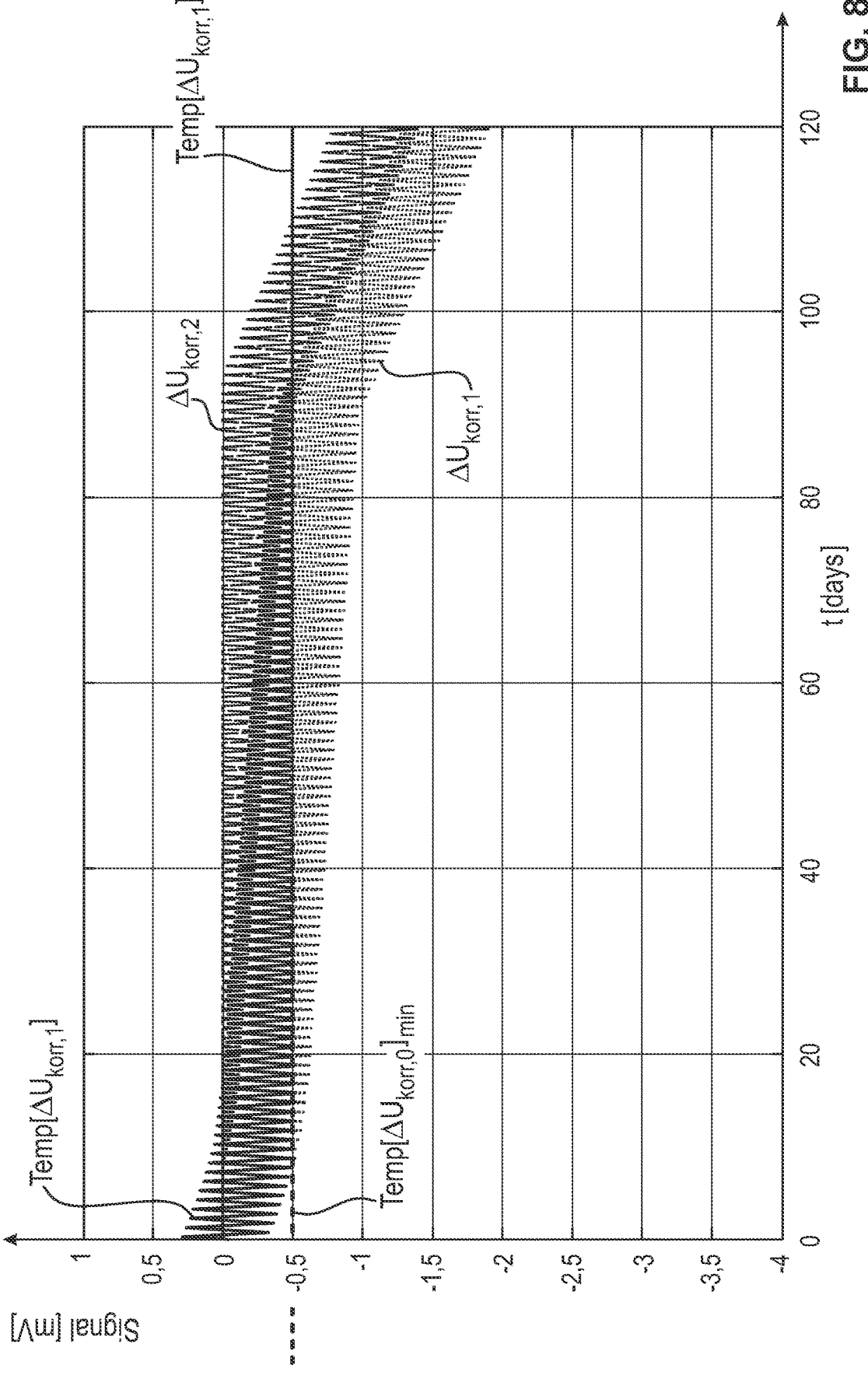
FIG. 8 is a graph showing a time course of FIG. 7 of the zero-point corrected bridge voltage adjusted for drift, as well as an estimated time course of the influence of the daily temperature variation and a time course of the zero-point corrected bridge voltage adjusted for drift and temperature influence.

FIG. 3 and FIG. 4 illustrate a first example, FIG. 5 and FIG. 6 illustrate a second example, and FIG. 7 and FIG. 8 illustrate a third example of time courses. As explained above, the first influencing variable is the aging of the gas detection device 100, and the estimated time course of the influence of the slower influencing variable, i.e., the course of the drift, is denoted by $Dr[\Delta U_{korr,0}]$. The faster influencing variable is the time-of-day dependent change in ambient temperature, and the estimated time course of the influence of the faster influencing variable is denoted $Temp[\Delta U_{korr,1}]$.

In the first example, the drift increases approximately linearly after a ramp-up phase, cf. FIG. 3. The smallest and the largest permissible change per time unit for $Dr[\Delta U_{korr,0}]$ are indicated. It was predefined that the estimation Temp $[\Delta U_{korr,1}]$ for the faster influencing variable takes at most a value of $Temp[\Delta U_{korr,0}]_{max}=+1.8$ mV. Therefore, the influence of the faster influencing variable was not fully compensated, which can be seen in the course of $\Delta U_{korr,2}$, cf. FIG. 4.

In the second and in the third example it was given that the estimate $Dr[\Delta U_{korr,0}]$ for the influence of the slower influencing variable takes at least a value of $Dr[\Delta U_{korr,0}]_{min}=-2$ mV. The estimate $Temp[\Delta U_{korr,1}]$ for the influence of the faster influencing variable assumes at least a value of $Temp[\Delta U_{korr,0}]_{min}=-0.5$ mV. The estimated time course $Dr[\Delta U_{korr,0}]$ for the influence of the drift reaches the lower threshold $Dr[\Delta U_{korr,0}]_{min}$ and then does not decrease further. Moreover, in the third example according to FIG. 7, the change in the estimated time course reaches the lower threshold $Dr[\Delta U_{korr,0}]_{min}$ of the change tolerance band. Therefore, the drift cannot be fully compensated. The estimated time course $Temp[\Delta U_{korr,1}]$ for the influence of the time-of-day dependent temperature variation also reaches the lower threshold $Temp[\Delta U_{korr,0}]_{min}$ and then does not decrease further.

Preferably, a message is output when several values of the estimated time course $Dr[\Delta U_{korr,0}]$ of the drift reach a threshold $Dr[\Delta U_{korr,0}]_{min}$ or $Dr[\Delta U_{korr,0}]_{max}$ of the specified wider value range. Indeed, this event means that the estimated influence of the drift has become so large that it has become necessary to check and/or to adjust the gas detection device 100. Therefore, in the second and in the third example, a message is issued after about 100 days. The reason: The estimated time course $Dr[\Delta U_{korr,0}]$ of the influence of the drift has reached the lower threshold $Dr[\Delta U_{korr,0}]_{min}$ and remains at this lower threshold.

In an alternative implementation, a model equation is predefined for the time course of the influence of at least one influencing variable. The model equation contains at least one model parameter. The model equation is, for example, a polynomial, in particular a straight line, a sine line or a spline. Preferably, a polynomial or a spline is used for the influence of the slower influencing variable, and a sinusoidal function is used for the influence of the faster influencing variable. The model parameter or each model parameter of the model equation is estimated, using for the estimation the sequence of measured values of the zero-point corrected detection variable $\Delta U_{korr,0}$ or the detection variable $\Delta U_{korr,1}$ additionally adjusted for drift.

When implemented as a spline, a sequence of successive time periods T(1), T(2), T(3), . . . is predefined. Each predetermined time period T(1), T(2), T(3), . . . is preferably so long that a combustible target gas occurs in the area to be monitored during at most half, particularly preferably during at most a quarter, of this time period T(j) and during the remainder of the time period the area to be monitored and thus the interior of the housing 1 are free of combustible target gas. On the other hand, each predetermined time period T(1), T(2), T(3), . . . is preferably as short as possible.

The value which the influencing variable to be estimated assumes at the beginning of the first period T(1) is known. For each time period T(j) a spline, for example a polynomial, is estimated, for which those measured values of the measurement value series are used which fall into this time period T(j). The given change tolerance band and the given value range are taken into account.

Figure 9:
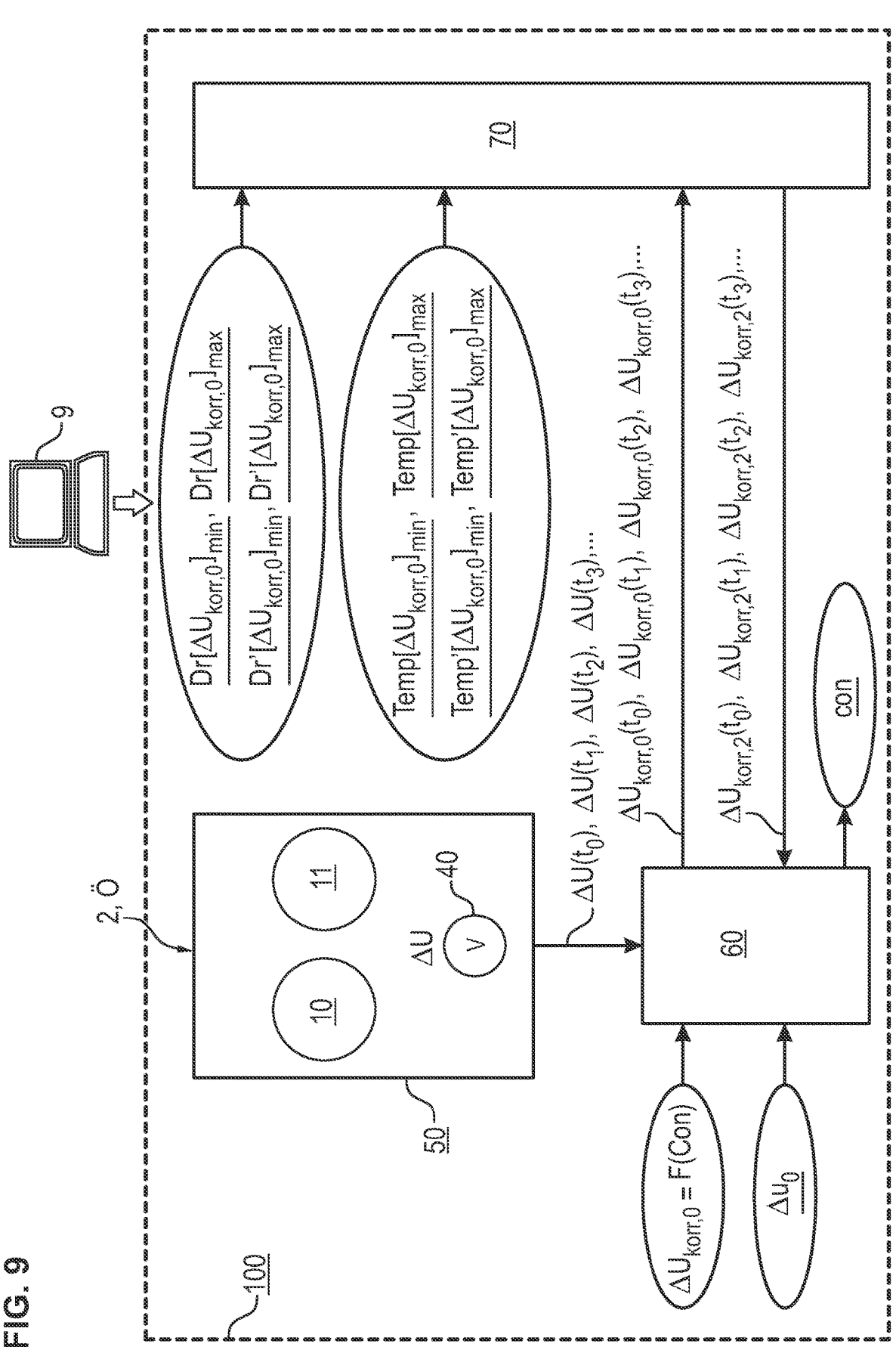
FIG. 9 is a schematic view showing the interaction of the sensor unit with the influencing variable estimator and the evaluation unit.

FIG. 9 illustrates the interaction of three components of the gas detection device 100 according to the invention. The following components are shown:
    the sensor unit 50, which comprises the detector 10, the compensator 11, the inner housing 1, the electrical lines 3, the electrical resistors R20 and R21, and the sensors 40 and 41, cf. FIG. 1,
    a signal processing evaluation unit 60,
    an influencing variable estimator 70 and
    an input unit 9.

The evaluation unit 60 has at least temporary read access to a data memory in which the functional relationship F and the zero point $\Delta u_0$ of the bridge voltage $\Delta U$ determined during an adjustment are stored. The evaluation unit 60 receives from the sensor unit 50 the measurement value series $\Delta U(t_0)$, $\Delta U(t_1)$, $\Delta U(t_2)$, $\Delta U(t_3)$, . . . and generates the zero-point corrected measurement value series $\Delta U_{korr,0}(t_0)$, $\Delta U_{korr,0}(t_1)$, $\Delta U_{korr,0}(t_2)$, $\Delta U_{korr,0}(t_3)$, . . . . The evaluation unit 60 may be a component of a control unit of the gas detection device 100.

The influencing variable estimator 70 preferably comprises a computer having a processor and at least one data memory. In the data memory or a data memory, the predetermined thresholds $Dr'[\Delta U_{korr,0}]_{min}$, $Dr'[\Delta U_{korr,0}]_{max}$ and $Temp'[\Delta U_{korr,0}]_{min}$, $Temp'[\Delta U_{korr,0}]_{max}$ of the change tolerance bands as well as the specified thresholds $Dr[\Delta U_{korr,0}]_{min}$, $Dr[\Delta U_{korr,0}]_{max}$ and $Temp[\Delta U_{korr,0}]_{min}$, $Temp[\Delta U_{korr,0}]_{max}$ of the value ranges are stored. With the help of the input unit 9, a user can enter the thresholds of the value ranges and the thresholds of the change tolerance bands. The same input unit 9 can be successively connected to different gas detection devices 100.

A program is stored in the or a data memory, which program is executed by the processor. When this program is executed, the influencing variable estimator 70 receives from the evaluation unit 60 the zero-point corrected measurement value series $\Delta U_{korr,0}(t_0)$, $\Delta U_{korr,0}(t_1)$, $\Delta U_{korr,0}(t_2)$, $\Delta U_{korr,0}(t_3)$, . . . . The influencing variable estimator 70 thus calculates, as just described, the zero-point corrected measurement value series $\Delta U_{korr,2}(t_0)$, $\Delta U_{korr,2}(t_1)$, $\Delta U_{korr,2}(t_2)$, $\Delta U_{korr,2}(t_3)$, . . . . This measurement value series is transmitted to the evaluation unit 60. The evaluation unit 60 decides whether the target gas or a given target gas is present, and/or calculates the concentration con of this target gas. Here, the evaluation unit 60 uses the relationship F and calculates the concentration con for a time t according to the calculation rule $con=F^{-1}[\Delta U_{korr,2}(t)]$.

The program of the influencing variable estimator 70 can be applied to different sensor units 50 and different evaluation units 60, even for sensor units 50 that apply different measurement principles. Therefore, it is sufficient to implement this program once and install it on each influencing variable estimator 70 used.

While specific embodiments of the invention have been shown and described in detail to illustrate the application of the principles of the invention, it will be understood that the invention may be embodied otherwise without departing from such principles.

LIST OF REFERENCE CHARACTERS

| | |
|---|---|
| 1 | Stable housing of the gas detection device 100, accommodates the detector 10 and the compensator 11, has the opening Ö, surrounded by the outer housing 4 |
| 2 | Flame retardant in the opening Ö, for example configured as a metal grid and/or sintered plate |
| 3 | Electrical line or line arrangement which connects the detector 10 and the compensator 11 to the voltage source 42 and thereby supplies them with electrical energy |
| 4 | Outer housing of the gas detection device 100, accommodates the sensor unit 50, the evaluation unit 60 and the influencing variable estimator 70, has the opening Ö |
| 5 | Compensator chamber, surrounds the compensator 11 |
| 8 | Detector chamber, surrounds the detector 10 |
| 9 | Input unit, allows a user to enter the value ranges and change tolerance bands |
| 10 | Detector, arranged in the detector chamber 8, comprises the electrically conductive and heated component 20, the ceramic coating 25 around the component 20, a coating 26 or embedding of a catalytic material, electrical contacts 24 and the mounting plate 27, configured as a pellistor |
| 11 | Compensator, comprises the electrically conductive and heated component 30, a ceramic jacket around the component 30, electrical contacts and a mounting plate, also configured as a pellistor |
| 20 | Electrically conductive and heated wire of the detector 10 |
| 24 | Electrical contacts for the wire 20 |
| 25 | Ceramic coating around the wire 20, provided with a catalytic coating 26 |
| 27 | Mounting plate holding the wire 20 and the ceramic coating 25 |
| 26 | Coating of the ceramic coating 25 from a catalytic material |
| 30 | Electrically conductive and heated wire of the compensator 11 |
| 40 | Voltage sensor, measures the electrical bridge voltage, preferably half the voltage difference $\Delta U = (U10 - U11)/2$ |
| 41 | Current intensity sensor, measures the current intensity I3 |
| 42 | Power supply unit of the gas detection device 100 |
| 50 | Sensor unit, includes detector 10, compensator 11, housing 1, electrical lead 3, sensors 40 and 41, and power supply unit 42 |
| 60 | Signal-processing evaluation unit, receives measured values from the sensor unit 50 and the influence-compensated detection variable $\Delta U_{korr,\,2}$ from the influencing variable estimator 70, determines the concentration con of the target gas |
| 70 | Influencing variable estimator, calculates the influence-compensated detection variable $\Delta U_{korr,\,2}$ |
| 100 | Gas detection device according to the invention, comprises the sensor unit 50, the evaluation unit 60 the influencing variable estimator 70, the power supply unit 42 and the outer housing 4 |
| Con | Variable sought: concentration of the combustible target gas |
| con | Value of the variable Con |
| $Dr[\Delta U_{korr,\,0}]$ | Estimated time course of the drift of the zero-point corrected detection variable $\Delta U_{korr,\,0}$, where the drift is caused by aging of the detector 10 and/or the compensator 11 and acts as the slower influencing variable |
| $Dr[\Delta U_{korr,\,0}]_{max}$ | Upper drift threshold: largest possible value for the influence of the slower influencing variable (drift due to aging of the gas detection device 100) on the zero-point corrected detection variable $\Delta U_{korr,\,0}$ |
| $Dr[\Delta U_{korr,\,0}]_{min}$ | Lower drift threshold: smallest possible value for the influence of the slower influencing variable (drift due to aging of the gas detection device 100) on the zero-point corrected detection variable $\Delta U_{korr,\,0}$ |

| | |
|---|---|
| Dr'[$\Delta U_{korr, 0}$] max | Upper drift change threshold: largest possible change per time unit of the influence of the slower influencing variable (drift due to aging of the gas detection device 100) on the detection variable $\Delta U_{korr, 0}$ |
| Dr'[$\Delta U_{korr, 0}$] min | Lower drift change threshold: smallest possible change per time unit of the influence of the slower influencing variable (drift due to aging of the gas detection device 100) on the zero-point corrected detection variable $\Delta U_{korr, 0}$ |
| $Ein_{max}$ | Upper threshold of the total value range: summed influence of all influencing variables |
| $Ein_{min}$ | Lower threshold of the total value range: summed influence of all influencing variables |
| $Ein'_{max}$ | Upper threshold of the total change tolerance band: sum of the upper thresholds of all change tolerance bands. |
| $Ein'_{min}$ | Lower threshold of the total change tolerance band: Sum of the lower thresholds of all change tolerance bands. |
| F | Empirically determined relationship: zero-point corrected bridge voltage $\Delta U_{korr, 2}$, adjusted for the influence of drift and temperature and zero-point corrected as a function of target gas concentration Con |
| G | gas sample from the area to be monitored |
| 13 | Current intensity of the current flowing through the line 3, measured by the current intensity sensor 41 |
| Ö | Opening in housings 1 and 4, accommodates the flame retardant 2 |
| R10 | Electrical resistance of the detector 10 |
| R11 | Electrical resistance of the compensator 11 |
| R20 | Component in the form of an electrical resistor, connected in parallel with the detector 10 |
| R21 | Component in the form of an electrical resistor, connected in parallel with the compensator 11 |
| $t_0, t_1, t_2, \ldots$ | Sequence of sampling times |
| $T(1), T(2), T(3), \ldots$ | Sequence of periods |
| Temp[$\Delta U_{korr, 1}$] | Estimated time course of the contribution of the time-of-day dependent ambient temperature to the zero-point corrected detection variable $\Delta U_{korr, 1}$ adjusted for the drift Dr[$\Delta U_{korr, 0}$], wherein ambient temperature acts as the faster influencing variable. |
| Temp[$\Delta U_{korr, 0}$]$_{max}$ | Upper threshold of the specified value range for the influence of the faster influencing variable on the zero-point corrected detection variable $\Delta U_{korr, 0}$ |
| Temp[$\Delta U_{korr, 0}$]$_{min}$ | Lower threshold of the specified value range for the influence of the faster influencing variable on the zero-point corrected detection variable $\Delta U_{korr, 0}$ |
| Temp'[$\Delta U_{korr, 0}$]$_{max}$ | Upper temperature change threshold: largest possible change per time unit of the influence of the faster influencing variable (temperature variations between day and night) on the zero-point corrected detection variable $\Delta U_{korr, 0}$ |
| Temp'[$\Delta U_{korr, 0}$]$_{min}$ | Lower temperature change threshold: smallest possible change per time unit of the influence of the faster influencing variable (temperature fluctuations between day and night) on the zero-point corrected detection variable $\Delta U_{korr, 0}$ |
| U10 | Electrical voltage applied to detector 10 |
| U11 | Electrical voltage applied to compensator 11 |
| $\Delta U$ | Bridge voltage, is equal to (U10 − U11)/2, measured by voltage sensor 40, acts as initial detection variable |
| $\Delta u_0$ | Zero point of the bridge voltage $\Delta U$, ideally occurs in a state free of combustible target gas, is determined empirically in advance |
| $\Delta U_{korr, 0}$ | Zero-point corrected bridge voltage, is adjusted for design-related differences between the detector 10 and the compensator 11, is equal to $\Delta U - \Delta u_0$ |
| $\Delta U_{korr, 0}(t_i)$ | Measured value of the zero-point corrected bridge voltage $\Delta U_{korr, 0}$ at the sampling time $t_i$ |
| $\Delta U_{korr, 1}$ | Corrected detection variable, obtained by compensating the influence of the slower influencing variable, aging, on the detection variable $\Delta U_{korr, 0}$, is equal to $\Delta U_{korr, 0} -$ Dr[$\Delta U_{korr, 0}$], and can also be called zero-point corrected and drift-adjusted bridge voltage |
| $\Delta U_{korr, 1}(t_i)$ | Measured value of the zero-point corrected and drift-adjusted bridge voltage $\Delta U_{korr, 1}$ at the sampling time $t_i$ |
| $\Delta U_{korr, 2}$ | The twice corrected detection variable, obtained by compensating both the influence of the slower influencing variable (aging) and the influence of the faster influencing variable (time-of-day dependent temperature variation) on the detection variable $\Delta U_{korr, 0}$, is equal to $\Delta U_{korr, 1} -$ Temp[$\Delta U_{korr, 1}$], can also be referred to as zero-point |

-continued

| | corrected bridge voltage adjusted for drift and time-of-day dependent temperature variation |
|---|---|
| $\Delta U_{korr,\,2}(t_i)$ | Measured value of the twice corrected detection variable $\Delta U_{korr,\,2}$ at the sampling time $t_i$ |

What is claimed is:

1. A gas detection device for monitoring a spatial area for a predetermined target gas, the gas detection device comprising:

a sensor unit comprising: a sensor having a detection variable affected by a concentration of the target gas in the area to be monitored; and a detection variable sensor configured to measure an indicator for the detection variable and by using measurement results for the detection variable, to generate a measurement value series which series describes a time course of the detection variable;

an influencing variable estimator configured to compensate by calculation both an influence of a slower influencing variable on the detection variable and an influence of a faster influencing variable on the detection variable, wherein the compensation is performed based on the measurement value series, and to thereby determine an influence-corrected detection variable, wherein the slower influencing variable and the faster influencing variable occur independently of the target gas; and an evaluation unit configured, depending on at least one value of the influence-corrected detection variable, to decide whether the target gas is present in the spatial area, and/or to determine the concentration of the target gas in the spatial area, wherein the gas detection device is configured to generate an alarm if the target gas is present or if the target gas concentration is above a predetermined concentration threshold and wherein an output unit is configured to output this alarm in a form that can be perceived by a human;

wherein a narrower change tolerance band is predefined for a possible change per time unit of the detection variable due to the influence of the slower influencing variable on the detection variable such that the change per time unit of the influence is within the narrower change tolerance band, wherein a wider change tolerance band is predefined for a possible change per time unit of the detection variable due to the influence of the faster influencing variable on the detection variable such that the change per time unit of the influence is within the wider change tolerance band, wherein the narrower change tolerance band is contained in but does not coincide with the wider change tolerance band, wherein a narrower value range is predefined for a possible variation of the detection variable due to the influence of the faster influencing variable on the detection variable such that the influence of the faster influencing variable is within the narrower value range, wherein the influencing variable estimator is configured to compensate for the influence of the slower influencing variable on the detection variable using the measurement value series to determine an estimated time course of the influence of the slower influencing variable such that the change per time unit of the estimated time course of the influence of slower influencing variable lies within the narrower change tolerance band, and to subtract the estimated time course of the slower influencing variable from the detection variable or from the detection variable corrected for the influence of the faster influencing variable, and wherein the influencing variable estimator is configured to compensate for the influence of the faster influencing variable on the detection variable using the measurement value series to determine an estimated time course of the influence of the faster influencing variable such that each value of the estimated time course lies in the narrower value range and a temporal change per time unit of the estimated time course of the influence of faster influencing variable lies in the wider change tolerance band, and to subtract the estimated time course of the influence of the faster influencing variable from the detection variable or from the detection variable corrected for the influence of the slower influencing variable.

2. A gas detection device according to claim 1, wherein:

each measured value of the measurement value series comprises a value of the detection variable at a sampling time;

the evaluation unit is configured to decide for at least one sampling time of the measurement value series, whether or not the target gas is present in the spatial area to be monitored at the sampling time;

the evaluation unit is configured to use for the decision the value of the influence-corrected detection variable at said sampling time, and the influencing variable estimator is configured to use the measured value of the measurement value series for that sampling time to estimate the time course of the influence of the slower influencing variable and to estimate the time course of the influence of the faster influencing variable only if it has been decided that no target gas is present at the sampling time.

3. A gas detection process for monitoring a spatial area for a predetermined target gas, the process comprising the steps of:

providing a gas detection device which comprises: a sensor unit comprising a sensor having a detection variable that is affected by a concentration of the target gas in the spatial area; and a detection variable sensor configured to measure an indicator for the detection variable;

providing a state in which a gas sample flows from the spatial area into an interior of the gas detection device;

with the detection variable sensor, repeatedly measuring an indicator for the detection variable, the detection variable being affected by the concentration of the target gas in the gas sample;

generating a measurement value series which describes the temporal course of the detection variable, the generation is performed using the results of the measurements of the detection variable;

using the measurement value series, compensating by calculation both an influence of a slower influencing variable and an influence of a faster influencing variable on the detection variable, to determine an influence-corrected detection variable, wherein the slower influencing variable and the faster influencing variable occur independently of the target gas;

deciding, depending on at least one value of the influence-corrected detection variable, whether the target gas is present in the spatial area, and/or determining the concentration of the target gas in the spatial area, wherein an alarm is generated if the target gas is present or if the target gas concentration is above a predetermined concentration threshold and wherein an output unit outputs this alarm in a form that can be perceived by a human;

wherein the step of compensating the influence of the slower influencing variable on the detection variable comprises the steps of:

predefining a narrower change tolerance band for a possible change per time unit of the detection variable due to the influence of the slower influencing variable on the detection variable; and determining an estimated time course of the influence of the slower influencing variable on the detection variable based on the measurement value series such that the temporal change per time unit of the estimated time course of the influence of the slower influencing variable lies in the narrower change tolerance band, and subtracting the estimated time course of the slower influencing variable from the detection variable or from the detection variable corrected for the influence of the faster influencing variable, and wherein the step of compensating for the influence of the faster influencing variable on the detection variable comprises the steps of:

predefining a wider change tolerance band for a possible change per time unit of the detection variable due to the influence of the faster influencing variable on the detection variable, wherein the narrower change tolerance band does not coincide with the wider change tolerance band and the narrower change tolerance band is contained in the wider change tolerance band;

predefining a narrower value range as the value range for a possible variation of the detection variable due to the influence of the faster influencing variable on the detection variable;

determining an estimated time course of the influence of the faster influencing variable on the detection variable based on the measurement value series such that each value of the estimated time course lies in the narrower value range, and the temporal change per time unit of the estimated time course of the influence of the faster influencing variable lies in the wider change tolerance band; and subtracting the estimated time course of the influence of the faster influencing variable from the detection variable or from the detection variable corrected for the influence of the slower influencing variable.

4. A process according to claim 3, wherein:

each measured value of the measurement value series comprises a value of the detection variable referring to a respective sampling time;

the process further comprises for at least one sampling time of the measurement value series:

deciding based on the value of the influence-corrected detection variable at that sampling time whether or not the target gas is present in the area to be monitored at that sampling time; and estimating the time course of the influence of the slower influencing variable and estimating the time course of the influence of the faster influencing variable based on the measured value of the measurement value series for the sampling time only if it was decided that no target gas is present at the sampling time.

5. A process according to claim 3, wherein if it has been decided that the target gas is present at the sampling time, a value determined by interpolation or extrapolation is used as the value of the respective estimated time course at the sampling time.

6. A process according to claim 3, wherein first the estimated time course of the influence of the slower influencing variable is subtracted from the detection variable and subsequently the estimated time course of the influence of the faster influencing variable is subtracted from the detection variable corrected for the influence of the slower influencing variable, whereby the step of subtracting the time course of the influence of the slower influencing variable from the detection variable provides a measurement value series compensated for the influence of the slower influencing variable, and the step of determining the estimated time course of the influence of the faster influencing variable on the detection variable is carried out using the measurement value series compensated for the influence of the slower influencing variable; or first the estimated time course of the influence of the faster influencing variable is subtracted from the detection variable and subsequently the estimated time course of the slower influencing variable is subtracted from the detection variable corrected for the influence of the faster influencing variable, whereby the step of subtracting the influence of the faster influencing variable from the detection variable provides a measurement value series compensated for the influence of the faster influencing variable, and the step of determining the estimated time course of the influence of the slower influencing variable on the detection variable is carried out using the measurement value series compensated for the influence of the faster influencing variable.

7. A process according to claim 3, wherein in a first phase, using the measurement value series, both the estimated time course of the influence of the slower influencing variable and the estimated time course of the influence of faster influencing variable are determined, and in a subsequent second phase, both the estimated time course of the slower influencing variable and the estimated time course of the faster influencing variable are subtracted from the detection variable.

8. A process according to claim 3, wherein:

another value range is predefined, namely for the influence of the slower influencing variable onto the detection variable;

the value range for the faster influencing variable is narrower than the value range for the slower influencing variable and is included in the value range for the slower influencing variable; and the estimated time course of the influence of the slower influencing variable is determined such that additionally each value of the estimated time course of the influence of the slower influencing variable lies in the value range for the slower influencing variable.

9. A process according to claim 8, wherein if a predefined number of values of the estimated time course of the slower influencing variable is equal to an upper threshold or equal to the lower threshold of the value range for the slower influencing variable, a message is generated and output in a form that can be perceived by a human.

10. A process according to claim 3, wherein:

the step of determining the influence-corrected detection variable comprises the additional step of compensating by calculation an influence of a third influencing variable on the detection variable based on the measurement value series;

the third influencing variable also occurs independently of the target gas;

the step of compensating the influence of the third influencing variable on the detection variable comprises the steps of:

predefining a third change tolerance band for a possible change per time unit of the detection variable due to the influence of the third influencing variable on the detection variable, wherein the wider change tolerance band is narrower than the third change tolerance band and is included in the third change tolerance band;

predefining a third value range for the influence of the third influencing variable on the detection variable, wherein the third value range is narrower than the value range for the faster influencing variable and is included in the value range for the faster influencing variable;

determining an estimated time course of the influence of the third influencing variable such that each value of the estimated time course of the influence of the third influencing variable lies in the third value range and the change per time unit of the estimated time course lies in the third change tolerance band; and subtracting the estimated time course of the influence of the third influencing variable from the detection variable or from the detection variable corrected for the slower and/or the faster influencing variable.

11. A process according to claim 3, wherein:

the sensor unit has an initial detection variable which is influenced by the concentration of the target gas in the area to be monitored; and a calibration is performed at least once, comprising the steps of:

establishing a state in which an environment and/or the interior of the gas detection device is free of the target gas;

measuring a value assumed by the initial detection variable for the established gas-free state;

determining a zero point based on the measured value of the initial detection variable; and using a difference between the initial detection variable and the zero point as the detection variable.

12. A process according to claim 3, wherein the evaluation unit is configured to generate an output based on the decision whether the target gas is present in the spatial area, and/or based on the determination of the concentration of the target gas in the spatial area.

13. A process according to claim 12, wherein based on the generated output, an output unit issues an alarm in a form that can be perceived by a human and/or indicates a value of the determined target gas concentration in a form that can be perceived by a human.

14. A gas detection device according to claim 1, wherein the evaluation unit is configured to generate an output based on the decision whether the target gas is present in the spatial area, and/or based on the determination of the concentration of the target gas in the spatial area.

15. A gas detection device according to claim 14, further comprising an output unit comprised by or connected to the gas detection device and operatively connected to the evaluation unit, wherein based on the generated output, the output unit issues an alarm in a form that can be perceived by a human and/or indicates a value of the determined target gas concentration in a form that can be perceived by a human.

16. A gas detection device according to claim 1, wherein:

a value range for the influence of the slower influencing variable on the detection variable is predefined;

the value range for the faster influencing variable is narrower than the value range for the slower influencing variable and is included in the value range for the slower influencing variable; and the estimated time course of the influence of the slower influencing variable is determined such that additionally each value of the estimated time course of the influence of the slower influencing variable lies in the value range for the slower influencing variable.

17. A gas detection device according to claim 1, wherein:

the evaluation unit is configured to access an initial detection variable of the sensor unit, which initial detection variable is influenced by the concentration of the target gas in the area to be monitored; and the evaluation unit is configured in a gas detection device state in which an environment and/or the interior of the gas detection device is free of the target gas, to provide a calibration, comprising:

measuring a value assumed by the initial detection variable for the established gas-free state;

determining a zero point based on the measured value of the initial detection variable; and using a difference between the initial detection variable and the zero point as the detection variable.

18. A gas detection device for monitoring a spatial area for a predetermined target gas, the gas detection device comprising:

a sensor unit comprising: a sensor having a detection variable affected by a concentration of the target gas in the area to be monitored; and a detection variable sensor configured to measure an indicator for the detection variable and to generate a detection variable measurement value series, which detection variable measurement value series describes a time course of the detection variable;

an influencing variable estimator comprising a processor and memory configured to determine an influence-corrected detection variable that at least partially corrects an influence of a slower influencing variable on the detection variable and at least partially corrects an influence of a faster influencing variable on the detection variable, wherein the slower influencing variable and the faster influencing variable occur independently of the target gas, wherein a narrower change tolerance band is predefined and stored in the memory for a possible change per time unit of the detection variable due to the influence of the slower influencing variable on the detection variable, wherein a wider change tolerance band is predefined and stored in the memory for a possible change per time unit of the detection variable due to the influence of the faster influencing variable on the detection variable and wherein the narrower change tolerance band is narrower than the wider change tolerance band and wherein the narrower change tolerance band is contained in the wider change tolerance band and wherein a narrower value range is predefined and stored in the memory for a possible variation of the detection variable due to the influence of the faster influencing variable on the detection variable, wherein the influencing variable estimator is configured to determine an estimated time course of the influence of the slower influencing variable with a recursive calculation based on the measurement value series such that the change per time unit of the determined estimated time course of the influence of slower influencing variable lies within the narrower variable change tolerance band, wherein the influencing variable estimator is configured to determine an estimated time course of the influence of the faster influencing variable with a recursive calculation based on the measurement value series such that each value of the determined estimated time course of the influence of the faster influencing variable lies in the narrower value range and the change per time unit of the determined estimated time course of the influence of the faster influencing variable lies in the wider change tolerance band, and wherein the influencing variable estimator is configured to determine the influence-corrected detection variable by:

subtracting the determined estimated time course of the influence of the slower influencing variable from the detection variable to form a detection variable corrected for the influence of the slower influencing variable and subtracting the determined estimated time course of the influence of the faster influencing variable from the detection variable corrected for the influence of the slower influencing variable; or subtracting the determined estimated time course of the influence of the faster influencing variable from the detection variable to form a detection variable corrected for the influence of the faster influencing variable and subtracting the determined estimated time course of the influence of the slower influencing variable from the detection variable corrected for the influence of the faster influencing variable; and an evaluation unit comprising the processor and memory or comprising another processor and memory, the evaluation unit being configured to decide whether the target gas is present in the spatial area, and/or to determine the concentration of the target gas in the spatial area based on at least one value of the influence-corrected detection variable, wherein the gas detection device is configured to generate an alarm if the target gas is present or if the target gas concentration is above a predetermined concentration threshold and wherein an output unit is configured to output this alarm in a form that can be perceived by a human.

19. A gas detection device according to claim 18, further comprising an output unit comprised by the gas detection device or connected to the gas detection device and operatively connected to the evaluation unit, wherein based on the generated output that indicates whether the target gas is present in the spatial area, and/or indicates the concentration of the target gas in the spatial area, the output unit issues an alarm in a form that can be perceived by a human and/or indicates a value of the determined target gas concentration in a form that can be perceived by a human.

20. A gas detection device according to claim 19, wherein:

a value range for the influence of the slower influencing variable on the detection variable is predefined;

the value range for the faster influencing variable is narrower than the value range for the slower influencing variable and is included in the value range for the slower influencing variable; and the estimated time course of the influence of the slower influencing variable is determined such that additionally each value of the estimated time course of the influence of the slower influencing variable lies in the value range for the slower influencing variable.

* * * * *